US009163080B2

(12) United States Patent
Morita et al.

(10) Patent No.: US 9,163,080 B2
(45) Date of Patent: Oct. 20, 2015

(54) ANTI-SINGLE-CHAIN TYPE IV COLLAGEN POLYPEPTIDE ANTIBODY, PHARMACEUTICAL DRUG, DIAGNOSTIC, PREVENTIVE, OR THERAPEUTIC DRUG FOR TUMOUR CONTAINING THE ANTIBODY

(71) Applicant: NIPPON KAYAKU KABUSHIKI KAISHA, Tokyo (JP)

(72) Inventors: Makoto Morita, Tokyo (JP); Arihiro Tomura, Tokyo (JP); Kan Saiga, Tokyo (JP); Toshihiko Hayashi, Tokyo (JP); Hidemitsu Sugihara, Tokyo (JP); Kazuhiro Tokunaka, Tokyo (JP); Takamichi Sato, Tokyo (JP); Yasutada Imamura, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 47 days.

(21) Appl. No.: 13/888,525

(22) Filed: May 7, 2013

(65) Prior Publication Data
US 2013/0224854 A1 Aug. 29, 2013

Related U.S. Application Data

(63) Continuation of application No. PCT/JP2011/075762, filed on Nov. 8, 2011.

(30) Foreign Application Priority Data

Nov. 10, 2010 (JP) ................................. 2010-252193

(51) Int. Cl.
| C07K 16/00 | (2006.01) |
| C07K 16/46 | (2006.01) |
| C07K 16/18 | (2006.01) |
| C07K 16/30 | (2006.01) |
| A61K 39/00 | (2006.01) |

(52) U.S. Cl.
CPC ................. *C07K 16/18* (2013.01); *C07K 16/30* (2013.01); *A61K 2039/505* (2013.01); *C07K 2317/34* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 5,859,205 A * | 1/1999 | Adair et al. ................. 530/387.3 |
| 7,365,167 B2 | 4/2008 | Watkins et al. |
| 2003/0113331 A1 | 6/2003 | Brooks et al. |
| 2008/0008707 A1 | 1/2008 | Freimark et al. |
| 2008/0260733 A1 | 10/2008 | Watkins et al. |
| 2010/0239581 A1 | 9/2010 | Joseloff et al. |

FOREIGN PATENT DOCUMENTS

| JP | 63-078067 | 4/1988 |
| JP | 02-001553 | 1/1990 |
| JP | 2007-112734 A | 5/2007 |
| WO | 03/046204 A2 | 6/2003 |

OTHER PUBLICATIONS

Rudikoff et al Single amino acid substitution altering antigen-binding specificity. Proc Natl Acad Sci U S A. Mar. 1982;79(6):1979-8.*
Klimka et al.,Human anti-CD30 recombinant antibodies by guided phage antibody selection using cell panning. British Journal of Cancer (2000) 83:252-260.*
Eduardo Padlan, Anatomy of the antibody molecule. Mol Immunol. Feb. 1994;31 (3):169-217.*
Kerbel (Cancer Biol Ther. Jul.-Aug. 2003;2(4 Suppl 1):S134-9).*
Paul, Fundamental Immunology, 3rd Edition, 1993, pp. 292-295.*
Beiboer et al., Guided selection of a pan carcinoma specific antibody reveals similar binding characteristics yet structural divergence between the original murine antibody and its human equivalent. J. Mol. Biol. 296:833-849 (2000).*
First Office Action issued by the State Intellectual Property of PRC on Jun. 16, 2014, for corresponding Chinese Application No. 201180054315.9.
First Office Action issued by the State Intellectual Property of PRC on Jun. 16, 2014, for corresponding Chinese Application No. 201180054315.9. (English Translation).
Accession No. BAD92883 GenBank Database, "COL4A1 protein variant, partial [*Home sapiens*]", Nov. 17, 2007.
Kohda et al., "High nephritogenicity of monoclonal antibodies belonging to IgG2a and IgG2b subclasses in rat anti-GBM nephritis", Kidney International, 2004, pp. 177-186, vol. 66, International Society of Nephrology.
Takahashi, S. et al., "Serum-dependent Secretion of Nondisulfide-bonded and Unfolded Type IV Collagen α Chains by Cultured Fetal Lung Fibroblasts", Connective Tissue, 1999, pp. 161-168, vol. 31.
Yoshikawa, K. et al., "Secretion of Non-Helical Collagenous Polypeptides of α1(IV) and α2(IV) Chains upon Depletion of Ascorbate by Cultured Human Cells", J. Biochem., 2001, pp. 929-936, vol. 129-issue No. 6.
D. Kajimura et al., "Non-helical type IV collagen polypeptides in human placenta", Biochemical and Biophysical Research Communications, 2004, pp. 11-16, vol. 314.
Thomas M. Mundel & Raghu Kalluri, "Type IV collagen-derived angiogenesis inhibitors", Microvascular Research, 2007, pp. 85-89, vol. 74.

(Continued)

*Primary Examiner* — Maher Haddad
(74) *Attorney, Agent, or Firm* — Pergament Gilman & Cepeda LLP; Milagros A. Cepeda; Edward D. Pergament

(57) ABSTRACT

A monoclonal antibody, wherein the monoclonal antibody specifically binds to a single-chain type IV collagen polypeptide, and wherein the monoclonal antibody is obtained by a hybridoma line of Anti NK-Antigen monoclonal antibody #141 having Accession No: FERM BP-11300.

14 Claims, 6 Drawing Sheets

(56) References Cited

OTHER PUBLICATIONS

Instruction manual of the type IV collagen assay kit "Panassay IV-C Latex", Daiichi Pure Chemicals Co., Ltd Mar. 2006 (revised edition).
Instruction manual of the type IV collagen assay kit "Panassay IV-C Latex", Daiichi Pure Chemicals Co., Ltd., Mar. 2006 (revised edition). (English Translation).
Obata, K. et al., "One step sandwich enzyme immunoassay for human type IV collagen using monoclonal antibodies", Clinica Chimica Acta, 1989, pp. 293-303, vol. 181.
M. Iwata et al., "Evidence for a Short Form of α1(IV) as a Major Polypeptide in Bovine Lens Capsule", J. Biochem., 1995, pp. 1298-1304, vol. 117.
International Search Report, dated Feb. 21, 2012, for corresponding International Patent Application No. PCT/JP2011/075762.

* cited by examiner

SEQUENCE LISTING

```
<160> NUMBER OF SEQ ID NOS: 42

<210> SEQ ID NO 1
<211> LENGTH: 458
<212> TYPE: DNA
<213> ORGANISM: Homo sapience

<400> SEQUENCE: 1
gaagtgcagc tggtggagtc tgggggaggc ttagtgaagc ctggagggtc cctgaaactc      60
tcctgtgcag cctctggatt cactttcact gactattaca tgtattgggt tcgccagact     120
ccggaaaaga ggctggagtg ggtcgcaacc atcagtgaag tggtagtta cacctactat      180 ccagacagtg tgaagggcg attcaccatc tccagagaca atgccaaaaa caacctgtac      240
ctgcaaatga gcagtctgaa gtctgaggac acagccatgt attactgtgc aagtccctat     300
tatggggacg gggggtttgc ttactgggc caagggactc tggtcactgt ctctgcagcc      360
aaaacaacac ccccatcagt ctatccactg gcccctgggt gtggagatac aactggttcc     420
tccgtgactc tgggatgcct ggtcaagggc tacttccc                            458

<210> SEQ ID NO 2
<211> LENGTH: 475
<212> TYPE: DNA
<213> ORGANISM: Homo sapience

<400> SEQUENCE: 2 gatgtttga tgacccaaac tccactctcc ctgcctgtca gtcttggaga tcaagcctcc      60
atctcttgca gatctagtca gagcattgta catagtgatg aaacaccta tttagaatgg     120 tacctacaga aaccaggcca gtctccaagg ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
ccgacgttcg gtggaggcac caagctggaa atcaaacggg ctgatgctgc accaactgta     360
tccatcttcc caccatccag tgagcagtta acatctggag gtgcctcagt cgtgtgcttc     420
ttgaacaact ctaccccaa agacatcaat gtcaagtgga gattgatgg cagtg          475

<210> SEQ ID NO 3
<211> LENGTH: 152
<212> TYPE: PRT
<213> ORGANISM: Homo sapience

<400> SEQUENCE: 3

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asp Tyr
            20                  25                  30

Tyr Met Tyr Trp Val Arg Gln Thr Pro Glu Lys Arg Leu Glu Trp Val
        35                  40                  45

Ala Thr Ile Ser Glu Gly Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95
```

Ala Ser Pro Tyr Tyr Gly Asp Gly Phe Ala Tyr Trp Gly Gln Gly
            100                 105                 110

Thr Leu Val Thr Val Ser Ala Ala Lys Thr Thr Pro Pro Ser Val Tyr
            115                 120                 125

Pro Leu Ala Pro Gly Cys Gly Asp Thr Thr Gly Ser Ser Val Thr Leu
            130                 135                 140

Gly Cys Leu Val Lys Gly Tyr Phe
145                 150

<210> SEQ ID NO 4
<211> LENGTH: 158
<212> TYPE: PRT
<213> ORGANISM: Homo sapience

<400> SEQUENCE: 4

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser
145                 150                 155

<210> SEQ ID NO 5
<211> LENGTH: 8
<212> TYPE: PRT
<213> ORGANISM: Homo sapience

<400> SEQUENCE: 5

Gly Phe Thr Phe Thr Asp Tyr Tyr
1               5

<210> SEQ ID NO 6
<211> LENGTH: 8
<212> TYPE: PRT
<213> ORGANISM: Homo sapience

<400> SEQUENCE: 6

Ile Ser Glu Gly Gly Ser Tyr Thr
1               5

<210> SEQ ID NO 7
<211> LENGTH: 12
<212> TYPE: PRT
<213> ORGANISM: Homo sapience

<400> SEQUENCE: 7

```
Ala Ser Pro Tyr Tyr Gly Asp Gly Gly Phe Ala Tyr
1               5                   10
```

<210> SEQ ID NO 8
<211> LENGTH: 11
<212> TYPE: PRT
<213> ORGANISM: Homo sapience

<400> SEQUENCE: 8

```
Gln Ser Ile Val His Ser Asp Gly Asn Thr Tyr
1               5                   10
```

<210> SEQ ID NO 9
<211> LENGTH: 3
<212> TYPE: PRT
<213> ORGANISM: Homo sapience

<400> SEQUENCE: 9

```
Lys Val Ser
1
```

<210> SEQ ID NO 10
<211> LENGTH: 9
<212> TYPE: PRT
<213> ORGANISM: Homo sapience

<400> SEQUENCE: 10

```
Phe Gln Gly Ser His Val Pro Pro Thr
1               5
```

<210> SEQ ID NO 11
<211> LENGTH: 5
<212> TYPE: PRT
<213> ORGANISM: Homo sapience

<400> SEQUENCE: 11

```
Asp Tyr Tyr Met Tyr
1               5
```

<210> SEQ ID NO 12
<211> LENGTH: 17
<212> TYPE: PRT
<213> ORGANISM: Homo sapience

<400> SEQUENCE: 12

```
Thr Ile Ser Glu Gly Gly Ser Tyr Thr Tyr Tyr Pro Asp Ser Val Lys
1               5                   10                  15

Gly
```

<210> SEQ ID NO 13
<211> LENGTH: 10
<212> TYPE: PRT
<213> ORGANISM: Homo sapience

<400> SEQUENCE: 13

```
Pro Tyr Tyr Gly Asp Gly Gly Phe Ala Tyr
1               5                   10
```

<210> SEQ ID NO 14
<211> LENGTH: 16
<212> TYPE: PRT
<213> ORGANISM: Homo sapience

<400> SEQUENCE: 14

```
Arg Ser Ser Gln Ser Ile Val His Ser Asp Gly Asn Thr Tyr Leu Glu
1               5                   10                  15

<210> SEQ ID NO 15
<211> LENGTH: 7
<212> TYPE: PRT
<213> ORGANISM: Homo sapience

<400> SEQUENCE: 15

Lys Val Ser Asn Arg Phe Ser
1               5

<210> SEQ ID NO 16
<211> LENGTH: 9
<212> TYPE: PRT
<213> ORGANISM: Homo sapience

<400> SEQUENCE: 16

Phe Gln Gly Ser His Val Pro Pro Thr
1               5

<210> SEQ ID NO 17
<211> LENGTH: 42
<212> TYPE: DNA
<213> ORGANISM: Artificial sequence
<220> FEATURE:
<223> OTHER INFORMATION: Forward primer

<400> SEQUENCE: 17
gtcgacgcca ccatggggcc ccggctcagc gtctggctgc tg                    42

<210> SEQ ID NO 18
<211> LENGTH: 38
<212> TYPE: DNA
<213> ORGANISM: Artificial sequence
<220> FEATURE:
<223> OTHER INFORMATION: Reverse primer

<400> SEQUENCE: 18
gcggccgctt atgttcttct catacagact tggcagcg                         38

<210> SEQ ID NO 19
<211> LENGTH: 36
<212> TYPE: DNA
<213> ORGANISM: Artificial sequence
<220> FEATURE:
<223> OTHER INFORMATION: Forward primer

<400> SEQUENCE: 19
ggtttcccag ggcagccagg ggccaagggc gacaga                           36

<210> SEQ ID NO 20
<211> LENGTH: 36
<212> TYPE: DNA
<213> ORGANISM: Artificial sequence
<220> FEATURE:
<223> OTHER INFORMATION: Reverse primer

<400> SEQUENCE: 20
cttcgcagcg gcccggctgt gctcctcgtg gagcag                           36

<210> SEQ ID NO 21
<211> LENGTH: 30
<212> TYPE: DNA
<213> ORGANISM: Artificial sequence
```

```
<220> FEATURE:
<223> OTHER INFORMATION: Forward primer

<400> SEQUENCE: 21
ggacctaaag gtgatccagg tataagtgga                                        30

<210> SEQ ID NO 22
<211> LENGTH: 36
<212> TYPE: DNA
<213> ORGANISM: Artificial sequence
<220> FEATURE:
<223> OTHER INFORMATION: Reverse primer

<400> SEQUENCE: 22
cttcgcagcg gcccggctgt gctcctcgtg gagcag                                 36

<210> SEQ ID NO 23
<211> LENGTH: 36
<212> TYPE: DNA
<213> ORGANISM: Artificial sequence
<220> FEATURE:
<223> OTHER INFORMATION: Forward primer

<400> SEQUENCE: 23
ggagatcaag ggatagcggg tttcccagga agccct                                 36

<210> SEQ ID NO 24
<211> LENGTH: 36
<212> TYPE: DNA
<213> ORGANISM: Artificial sequence
<220> FEATURE:
<223> OTHER INFORMATION: Reverse primer

<400> SEQUENCE: 24
cttcgcagcg gcccggctgt gctcctcgtg gagcag                                 36

<210> SEQ ID NO 25
<211> LENGTH: 42
<212> TYPE: DNA
<213> ORGANISM: Artificial sequence
<220> FEATURE:
<223> OTHER INFORMATION: Forward primer

<400> SEQUENCE: 25
gtcgacgcca ccatggggcc ccggctcagc gtctggctgc tg                          42

<210> SEQ ID NO 26
<211> LENGTH: 40
<212> TYPE: DNA
<213> ORGANISM: Artificial sequence
<220> FEATURE:
<223> OTHER INFORMATION: Reverse primer

<400> SEQUENCE: 26
gcggccgcga cttttcacct cgcagccctg ggatgcctat                             40

<210> SEQ ID NO 27
<211> LENGTH: 42
<212> TYPE: DNA
<213> ORGANISM: Artificial sequence
<220> FEATURE:
<223> OTHER INFORMATION: Forward primer

<400> SEQUENCE: 27
gtcgacgcca ccatggggcc ccggctcagc gtctggctgc tg                          42
```

```
<210> SEQ ID NO 28
<211> LENGTH: 30
<212> TYPE: DNA
<213> ORGANISM: Artificial sequence
<220> FEATURE:
<223> OTHER INFORMATION: Reverse primer

<400> SEQUENCE: 28
tggcaagccc attccaccaa cagatccttt                                    30

<210> SEQ ID NO 29
<211> LENGTH: 30
<212> TYPE: DNA
<213> ORGANISM: Artificial sequence
<220> FEATURE:
<223> OTHER INFORMATION: Forward primer

<400> SEQUENCE: 29
ggaacacctg gagagaaagg tgtgcctggc                                    30

<210> SEQ ID NO 30
<211> LENGTH: 36
<212> TYPE: DNA
<213> ORGANISM: Artificial sequence
<220> FEATURE:
<223> OTHER INFORMATION: Reverse primer

<400> SEQUENCE: 30
cttcgcagcg gcccggctgt gctcctcgtg gagcag                             36

<210> SEQ ID NO 31
<211> LENGTH: 30
<212> TYPE: DNA
<213> ORGANISM: Artificial sequence
<220> FEATURE:
<223> OTHER INFORMATION: Forward primer

<400> SEQUENCE: 31
ggagatcaag ggatagcggg tttcccagga                                    30

<210> SEQ ID NO 32
<211> LENGTH: 30
<212> TYPE: DNA
<213> ORGANISM: Artificial sequence
<220> FEATURE:
<223> OTHER INFORMATION: Reverse primer

<400> SEQUENCE: 32
tggcaagccc attccaccaa cagatccttt                                    30

<210> SEQ ID NO 33
<211> LENGTH: 30
<212> TYPE: DNA
<213> ORGANISM: Artificial sequence
<220> FEATURE:
<223> OTHER INFORMATION: Forward primer

<400> SEQUENCE: 33
gggcaggcag gcccacctgg cataggcatc                                    30

<210> SEQ ID NO 34
<211> LENGTH: 30
<212> TYPE: DNA
<213> ORGANISM: Artificial sequence
<220> FEATURE:
<223> OTHER INFORMATION: Reverse primer
```

-continued

<400> SEQUENCE: 34
tggcaagccc attccaccaa cagatccttt                                   30

<210> SEQ ID NO 35
<211> LENGTH: 30
<212> TYPE: DNA
<213> ORGANISM: Artificial sequence
<220> FEATURE:
<223> OTHER INFORMATION: Forward primer

<400> SEQUENCE: 35
ggagatcaag ggatagcggg tttcccagga                                   30

<210> SEQ ID NO 36
<211> LENGTH: 30
<212> TYPE: DNA
<213> ORGANISM: Artificial sequence
<220> FEATURE:
<223> OTHER INFORMATION: Reverse primer

<400> SEQUENCE: 36
tttctctcct tttgcacctt tgtctccagg                                   30

<210> SEQ ID NO 37
<211> LENGTH: 11
<212> TYPE: PRT
<213> ORGANISM: Homo sapience

<400> SEQUENCE: 37

Gly Ile Gly Ile Pro Gly Leu Arg Gly Glu Lys
1               5                   10

<210> SEQ ID NO 38
<211> LENGTH: 10
<212> TYPE: PRT
<213> ORGANISM: Homo sapience

<400> SEQUENCE: 38

Ile Gly Ile Pro Gly Leu Arg Gly Glu Lys
1               5                   10

<210> SEQ ID NO 39
<211> LENGTH: 9
<212> TYPE: PRT
<213> ORGANISM: Homo sapience

<400> SEQUENCE: 39

Gly Ile Pro Gly Leu Arg Gly Glu Lys
1               5

<210> SEQ ID NO 40
<211> LENGTH: 10
<212> TYPE: PRT
<213> ORGANISM: Homo sapience

<400> SEQUENCE: 40

Gly Ile Gly Ile Pro Gly Leu Arg Gly Glu
1               5                   10

<210> SEQ ID NO 41
<211> LENGTH: 9
<212> TYPE: PRT
<213> ORGANISM: Homo sapience -continued

```
<400> SEQUENCE: 41

Gly Ile Gly Ile Pro Gly Leu Arg Gly
1               5

<210> SEQ ID NO 42
<211> LENGTH: 8
<212> TYPE: PRT
<213> ORGANISM: Homo sapience

<400> SEQUENCE: 42

Gly Ile Gly Ile Pro Gly Leu Arg
1               5
```

US 9,163,080 B2

ANTI-SINGLE-CHAIN TYPE IV COLLAGEN POLYPEPTIDE ANTIBODY, PHARMACEUTICAL DRUG, DIAGNOSTIC, PREVENTIVE, OR THERAPEUTIC DRUG FOR TUMOUR CONTAINING THE ANTIBODY

CROSS-REFERENCE TO RELATED APPLICATION

This is a continuation application of PCT/JP2011/075762, filed on Nov. 8, 2011, which claims priority to Japanese Patent Application No. 2010-252193, filed on Nov. 10, 2010, all of which are hereby incorporated by reference in their entirely.

BACKGROUND OF THE INVENTION

1. Field of the Invention

The present invention relates to a monoclonal antibody that binds to a single-chain type IV collagen polypeptide secreted as a single-chain form of a type IV collagen gene product and suppresses the growth of tumor tissues expressing the single-chain type IV collagen polypeptide. The present invention also relates to a pharmaceutical drug and a diagnostic, preventive, or therapeutic drug for tumor containing the monoclonal antibody.

2. Description of the Related Art

Living tissues are composed of cells, which are units of life, and extracellular matrices present around or between the cells. The extracellular matrices are large protein complexes composed mainly of sugar-modified proteins such as collagen, laminin, elastin and proteoglycan. The collagen accounts for approximately 30% of biological proteins and is abundantly found in connective tissues. Also, the collagen constitutes basement membranes at the boundary between epithelial and connective tissues or at the boundary between endothelial and connective tissues. The functions of the extracellular matrices are known to be involved in the control of cell growth and/or differentiation. The interaction between the extracellular matrices and cells has been shown to be important for the development, repair, regeneration, or the like of normal tissues.

This interaction between the extracellular matrices and cells has also been shown to play an important role in tumor cell growth and angiogenesis during tumor formation. Tumor cells reconstruct an extracellular microenvironment by the repetitive degradation and remodeling of the extracellular matrices. As a result, the growth of the tumor cells or the formation of new blood vessels is promoted to allow tumor tissues to grow. Also, the invasion and/or metastasis of the tumor cells are known to occur due to the degradation of such remodeled extracellular matrices.

The collagen is known to include 20 or more types differing in genotype. For example, mainly type I collagen is present in connective tissues composed of fibroblasts, interstitial cells, and the like, while mainly type IV collagen is present in basement membranes.

The type IV collagen is secreted from various cells such as epithelial cells and endothelial cells, in addition to fibroblasts or interstitial cells. The type IV collagen molecules thus secreted are considered to associate with one another to construct the basement membrane skeleton having a mesh structure. The basement membranes of normal tissues are present at the boundary between epithelial and interstitial tissues, the boundary between endothelial and interstitial tissues, or the like and regulate tissue morphology and functions.

The collagen molecule has a loose right-handed triple helix structure composed of three polypeptide chains together, each of which has the conformation of a left-handed helix. The type IV collagen includes 6 genotypes. α1 to α6 polypeptide chains derived from these 6 genes are known and thought to be variously combined to form three or more types of molecular species. The most widely found basement membranes are constituted of aggregates of the type IV collagen molecules each having two α1 polypeptide chains and one α2 polypeptide chain cross-linked through intermolecular disulfide bonds. By contrast, the type IV collagen molecules composed of α3 to α6 polypeptide chains are found only in the basement membranes of a limited number of tissues.

As described above, the type IV collagen refers to a trimer molecule having a triple helix structure formed by three a polypeptide chains cross-linked through intermolecular disulfide bonds, or an aggregate of these trimer molecules. In general, the type IV collagen is known to be extracellularly secreted as trimer molecules to form aggregates outside the cell. However, the present inventors have found that cultured human cells secrete the type IV collagen as well as its single polypeptide chain (hereinafter, also referred to as a "single-chain type IV collagen polypeptide") that neither has an intermolecular disulfide bond nor takes a helix structure (see Takahashi, S. et al., Connective Tissue (1999) vol. 31; pp. 161-168). Particularly, cells cultured in a vitamin C-free medium produce the single-chain type IV collagen polypeptide in a much larger amount than that of the type IV collagen (see Yoshikawa, K. et al., J. Biochem. (2001) vol. 129; pp. 929-936). Also, the type IV collagen is known to undergo degradation by a protein-degrading enzyme (gelatinase, matrix metalloprotease-2, etc.). Because of lacking a helix structure, the single-chain type IV collagen polypeptide is more susceptible to degradation by a degrading enzyme than the type IV collagen having a triple helix structure. Accordingly, it has been assumed that the full-length single-chain type IV collagen polypeptide is difficult to detect in vivo. Nevertheless, the present inventors have found the single-chain type IV collagen polypeptide in human placenta (see Kajimura, D. et al., Biochemical and Biophysical Research Communications (2004) vol. 314; pp. 11-16).

The present inventors have further revealed that the single-chain type IV collagen polypeptide secreted from cells undergoes a posttranslational modification different from that of the type IV collagen. Proline hydroxylation and lysine hydroxylation in the type IV collagen are known to participate in the formation and/or stabilization of the triple helix structure, whereas the degrees of proline hydroxylation and lysine hydroxylation in the single-chain type IV collagen polypeptide are lower compared with the type IV collagen. In addition, the single-chain type IV collagen polypeptide reacts with *Agaricus bisporus* agglutinin (ABA) lectin that recognizes a sugar chain Galβ1-3GalNAc, whereas the type IV collagen does not react with ABA lectin.

As described above, the single-chain type IV collagen polypeptide has a chemical structure different from that of the type IV collagen or a polypeptide resulting from the denaturation thereof. The single-chain type IV collagen polypeptide is thus presumed to have biological functions different from those of the type IV collagen.

Solid tumor requires new blood vessels for its growth. For this reason, the inhibition of angiogenesis is one of methods for inhibiting tumor growth. The type IV collagen has collagenous and non-collagenous regions. Arresten, a polypeptide contained in the C-terminal non-collagenous region, reportedly inhibits lumen formation and inhibits angiogenesis, resulting in the suppression of tumor growth (see Thomas M. Mundel et al., Microvascular Research (2007) vol. 74; pp. 85-89).

JK199 (see Japanese Patent Application Laid-Open (JP-A) No. 63-78067) and antibodies contained in assay kits for the type IV collagen in serum (see Instruction manual of the type IV collagen assay kit "Panassay IV-C Latex"; Daiichi Pure Chemicals Co., Ltd. (2006 revised edition); Obata, K. et al., Clinica Chimica Acta 181, pp. 293-304, 1989; and JP-A No. 2-1553) have been reported as monoclonal antibodies against the type IV collagen.

In addition, an antibody acting on a "cryptic collagen site" (see JP-A No. 2009-240324) has been reported as a monoclonal antibody against denatured type IV collagen. However, it has been neither disclosed nor suggested that these antibodies recognize the single-chain type IV collagen polypeptide that is extracellularly secreted and stably present.

Meanwhile, JK132 (see Takahashi, S. et al., Connective Tissue (1999) vol. 31; pp. 161-168 and Iwata, M. et al., Journal of Biochemistry (1995) vol. 117 (6); pp. 1298-1304) has been reported to recognize the single-chain type IV collagen polypeptide, as an antibody recognizing the single-chain type IV collagen polypeptide. Unfortunately, these reports have not revealed the biological role of the single-chain type IV collagen polypeptide or its relation to cancer. Thus, it has been neither disclosed nor suggested that a pharmaceutical drug containing an antibody against the single-chain type IV collagen polypeptide is useful as diagnostic and therapeutic drugs for tumor.

SUMMARY OF THE INVENTION

An object of the present invention is to solve the conventional problems described above and provide a monoclonal antibody excellent in tumor tissue selectivity, a pharmaceutical drug containing the monoclonal antibody, and a diagnostic, preventive, or therapeutic drug for tumor useful in the treatment or diagnosis of tumor, containing the monoclonal antibody.

The present inventors have conducted diligent studies to attain the object and consequently completed the present invention by finding that a single-chain type IV collagen polypeptide is highly expressed in human cancer cell lines, cancer tissues of cancer-bearing animals, and human clinical tumor; and a monoclonal antibody specifically binding to the single-chain type IV collagen polypeptide suppresses the growth of the cancer tissues of the cancer-bearing animals.

The present invention is based on the findings obtained by the present inventors, and means for solving the problems are as follows.

The invention provides a monoclonal antibody, wherein the monoclonal antibody specifically binds to a single-chain type IV collagen polypeptide, and wherein the monoclonal antibody is produced by a hybridoma line of Anti NK-Antigen monoclonal antibody #141 (Accession No: FERM BP-11300).

The monoclonal antibody according to the present invention, wherein the monoclonal antibody contains an H chain containing at least one amino acid sequence selected from amino acid sequences represented by SEQ ID NOs: 5 to 7; and an L chain containing at least one amino acid sequence selected from amino acid sequences represented by SEQ ID NOs: 8 to 10.

The monoclonal antibody according to the present invention, wherein the monoclonal antibody contains an H chain containing at least one amino acid sequence selected from amino acid sequences represented by SEQ ID NOs: 11 to 13; and an L chain containing at least one amino acid sequence selected from amino acid sequences represented by SEQ ID NOs: 14 to 16.

The monoclonal antibody according to the present invention, wherein the monoclonal antibody recognizes an epitope containing an amino acid sequence represented by GIGIPGLRG (SEQ ID NO: 41).

A monoclonal antibody, comprising at least one complementarity determining region (CDR) of the monoclonal antibody according to the present invention.

A monoclonal antibody, comprising an H chain containing at least one amino acid sequence selected from amino acid sequences represented by SEQ ID NOs: 5 to 7; and an L chain containing at least one amino acid sequence selected from amino acid sequences represented by SEQ ID NOs: 8 to 10, the H and L chains being contained in the monoclonal antibody according to the present invention.

A monoclonal antibody, comprising an H chain containing at least one amino acid sequence selected from the amino acid sequences represented by SEQ ID NOs: 11 to 13; and an L chain containing at least one amino acid sequence selected from the amino acid sequences represented by SEQ ID NOs: 14 to 16, the H and L chains being contained in the monoclonal antibody according to the present invention.

A monoclonal antibody, wherein the monoclonal antibody recognizes an epitope containing an amino acid sequence represented by GIGIPGLRG (SEQ ID NO: 41), the epitope being recognized by the monoclonal antibody according to the present invention.

The monoclonal antibody according to the present invention, wherein the monoclonal antibody is humanized.

A monoclonal antibody, comprising at least one complementarity determining region (CDR) of the monoclonal antibody according to the present invention, and a human antibody, wherein the at least one complementarity determining region (CDR) is grafted to the human antibody.

A monoclonal antibody, comprising an H chain containing at least one amino acid sequence selected from amino acid sequences represented by SEQ ID NOs: 5 to 7; and an L chain containing at least one amino acid sequence selected from amino acid sequences represented by SEQ ID NOs: 8 to 10.

A monoclonal antibody, comprising an H chain containing at least one amino acid sequence selected from amino acid sequences represented by SEQ ID NOs: 11 to 13; and an L chain containing at least one amino acid sequence selected from the amino acid sequences represented by SEQ ID NOs: 14 to 16.

A monoclonal antibody, wherein the monoclonal antibody recognizes an epitope containing an amino acid sequence represented by GIGIPGLRG (SEQ ID NO: 41).

The monoclonal antibody according to the present invention, wherein the monoclonal antibody is humanized.

A hybridoma line, wherein the hybridoma line is Anti NK-Antigen monoclonal antibody #141 (Accession No: FERM BP-11300).

A pharmaceutical drug comprising a monoclonal antibody according to the present invention.

A diagnostic, preventive, or therapeutic drug for tumor, comprising a monoclonal antibody according to the present invention.

The diagnostic, preventive, or therapeutic drug for tumor according to the present invention, wherein the tumor is tumor containing cancer cells expressing a single-chain type IV collagen polypeptide.

A partial structure of the monoclonal antibody according to the present invention, wherein the partial structure contains at least one complementarity determining region (CDR) of the monoclonal antibody, and wherein the at least one CDR contains: at least one amino acid sequence selected from amino acid sequences represented by SEQ ID NOs: 5 to 7; and at least one amino acid sequence selected from amino acid sequences represented by SEQ ID NOs: 8 to 10.

A partial structure of the monoclonal antibody according to the present invention, wherein the partial structure contains at least one complementarity determining region (CDR) of the monoclonal antibody, and wherein the at least one CDR contains at least one amino acid sequence selected from amino acid sequences represented by SEQ ID NOs: 11 to 13; and at least one amino acid sequence selected from amino acid sequences represented by SEQ ID NOs: 14 to 16.

The present invention can solve the conventional problems described above and attain the object. Specifically, the present invention can provide a monoclonal antibody excellent in tumor tissue selectivity, a pharmaceutical drug containing the monoclonal antibody, and a diagnostic, preventive, or therapeutic drug for tumor useful in the treatment of diagnosis of tumor, containing the monoclonal antibody.

DETAILED DESCRIPTION OF THE INVENTION

Figure 1:
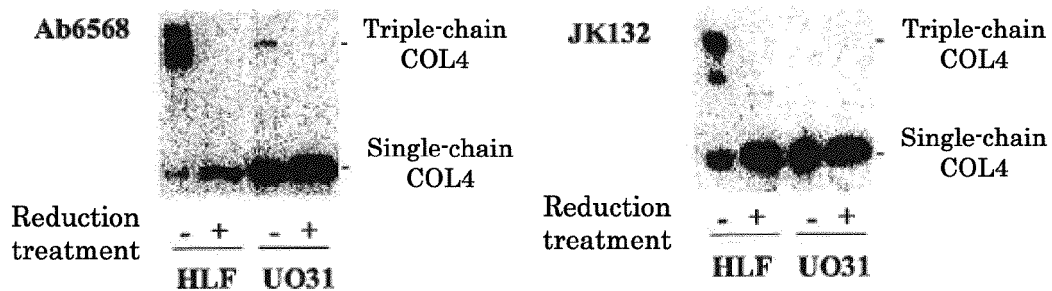
FIG. 1 is a diagram showing one example of the expression of the single-chain type IV collagen polypeptide in a tumor cell line (human liver cancer cell line HLF or human kidney cancer cell line UO31). Both JK132 and Ab6586 (manufactured by Abcam plc.) are antibodies recognizing the single-chain type IV collagen polypeptide in Western blotting. The term "triple-chain COL4" represents SDS-denatured type IV collagen that maintains its intermolecular disulfide bonds among the three chains. The term "single-chain COL4" represents the single-chain type IV collagen polypeptide. The mark "−" for reduction treatment represents that a buffer solution for electrophoresis samples is free from 2-mercaptoethanol. The mark "+" for reduction treatment represents that a buffer solution for electrophoresis samples contains 2-mercaptoethanol.

The monoclonal antibody of the present invention is hereinafter, also referred to as an "anti-single-chain type IV collagen polypeptide antibody", "NK46141", or the like.

According to a first embodiment, the monoclonal antibody of the invention specifically binds to a single-chain type IV collagen polypeptide, the antibody being produced by a hybridoma line of Anti NK-Antigen monoclonal antibody #141 (Accession No: FERM BP-11300). The hybridoma line of Anti NK-Antigen monoclonal antibody #141 was internationally deposited with International Patent Organism Depositary, National Institute of Advanced Industrial Science and Technology (receipt date: Oct. 5, 2010).

According to a second embodiment, the monoclonal antibody of the invention comprises an H chain containing at least one amino acid sequence selected from the amino acid sequences represented by SEQ ID NOs: 5 to 7, and an L chain containing at least one amino acid sequence selected from the amino acid sequences represented by SEQ ID NOs: 8 to 10, or a monoclonal antibody containing an H chain containing at least one amino acid sequence selected from the amino acid sequences represented by SEQ ID NOs: 11 to 13, and an L chain containing at least one amino acid sequence selected from the amino acid sequences represented by SEQ ID NOs: 14 to 16.

In a third embodiment, the monoclonal antibody of the present invention recognizes an epitope containing the amino acid sequence represented by GIGIPGLRG (SEQ ID NO: 41).

The monoclonal antibodies of the present invention specifically bind to the single-chain type IV collagen polypeptide. The monoclonal antibodies of the present invention may be the same as or different from one another as long as these monoclonal antibodies have their respective features described above.

In the present invention, the "single-chain type IV collagen polypeptide" refers to a protein secreted in a single-chain form of a type IV collagen gene product from cells. Typically, the "type IV collagen" refers to a protein having a triple helix structure composed of three type IV collagen gene products cross-linked through intermolecular disulfide bonds. By contrast, the "single-chain type IV collagen polypeptide" has no such intermolecular disulfide bond.

The single-chain type IV collagen polypeptide (molecular weight: approximately 180 kDa) has a chemical structure different from that of a monomer obtained by the reduction of the type IV collagen (molecular weight: approximately 500 kDa) or a polypeptide resulting from the denaturation thereof. The single-chain type IV collagen polypeptide has a lower proportion of hydroxylated proline residues or hydroxylated lysine residues than that of the type IV collagen. Unlike the type IV collagen, the single-chain type IV collagen polypeptide has a sugar chain Galβ1-3GalNAc that is recognized by *Agaricus bisporus* agglutinin (ABA) lectin. The single-chain type IV collagen polypeptide also includes even genetically polymorphic forms, gene variants, splicing variants, and posttranslational modification variants thereof.

The cells producing the single-chain type IV collagen polypeptide may be naturally occurring cells or may be recombinant cells containing a gene encoding the single-chain type IV collagen polypeptide. The cells are not limited by any means as long as these cells produce the single-chain type IV collagen polypeptide. The recombinant cells can be obtained by an approach known in the art.

In the present invention, the "antibody specifically binding to a single-chain type IV collagen polypeptide" (anti-single-chain type IV collagen polypeptide antibody) is not limited by its origin, type, shape, etc., as long as the antibody specifically recognizes the single-chain type IV collagen polypeptide without recognizing the type IV collagen. The antibody is not limited to a monoclonal antibody. Even a polyclonal antibody is also included in the scope the present invention.

The polyclonal antibody can be obtained by an approach known in the art from the serum immunoglobulin fraction of an animal sensitized with the single-chain type IV collagen polypeptide. In this regard, the animal to be sensitized is not limited by its species as long as the animal produces the polyclonal antibody.

The anti-single-chain type IV collagen polypeptide antibody according to the first embodiment can be the anti-single-chain type IV collagen polypeptide antibody itself that is produced by the hybridoma line of Anti NK-Antigen monoclonal antibody #141 (Accession No: FERM BP-11300). In addition, for example, a chimeric antibody, a humanized antibody, a human antibody, or a mouse antibody containing a partial structure of the anti-single-chain type IV collagen polypeptide antibody is also included in the scope of the present invention. Among these antibodies, a humanized antibody or a human antibody is particularly preferred.

The partial structure is not particularly limited as long as the partial structure is a portion of the anti-single-chain type IV collagen polypeptide antibody specifically recognizing the single-chain type IV collagen polypeptide. The partial structure can be selected appropriately according to the purpose. Examples thereof include partial structures including Fab, F(ab')₂, variable regions (V regions), complementarity determining regions (CDRs), and single-chain antibodies (scFvs), which bind to the antigen (single-chain type IV collagen polypeptide).

The "chimeric antibody" means an antibody containing regions derived from two or more different antibodies. In one embodiment, the chimeric antibody contains a region derived from the V regions of the anti-single-chain type IV collagen polypeptide antibody. In another embodiment, the chimeric antibody contains V regions derived from a plurality of anti-single-chain type IV collagen polypeptide antibodies.

The "human antibody" refers to an antibody having V regions derived from a human immunoglobulin sequence. A technique for preparing the human antibody is also known in the art, and a preparation method based on a gene engineering approach has already been established.

The "humanized antibody" refers to an antibody prepared by grafting one or more CDRs of the antibody of a non-human mammal, for example, a mouse onto CDRs of a human antibody. The general gene recombination approach thereof is also known (see EP Patent Application Publication No. EP125023 and International Publication No. WO 96/02576).

Specifically, a known method involves: designing a DNA sequence encoding mouse antibody CDRs linked with human antibody framework regions (FRs); synthesizing the DNA sequence by PCR using several oligonucleotide primers prepared to have portions overlapping with the terminal regions of both CDRs and FRs; and producing the humanized antibody using the synthesized DNA sequence (see the method described in International Publication No. WO 98/13388).

The human antibody FRs to be linked via the CDRs are selected from those permitting formation of the antigen-binding sites of the antibody with high binding affinity for the antigen. If necessary, the amino acids of FRs in the antibody variable region may be substituted so that the antigen-binding sites of the antibody with high binding affinity for the antigen can be formed.

The CDRs mean nonconsecutive antigen-binding sites found in the variable regions of both heavy chain and light chain polypeptides. These particular regions are known in the art and have been described by Kabat et al. (J. Biol. Chem., 252: 6609-6616 (1977)), Kabat et al. (United States Department of Health and Human Services (HHS), "Sequences of proteins of immunological interest" (1991)), Chothia et al. (J. Mol. Biol., 196; 901-917 (1987)), and MacCallum et al. (J. Mol. Biol., 262; 732-745 (1996)).

These regions are also available from some databases such as the IMGT/LIGM-DB database [described in Giudicelli et al., 2006, Nucleic Acids Research 34 (Database Issue); D781-D784; and Lefranc et al., 1995, LIGM-DB/IMGT: An Integrated Database of Ig and TcR, Part of the Immunogenetics Database. Annual of the New York Academy of Science 764

(1), 47-47 doi; 10.1111/j.1749-6632.1995.tb55805.x (http://www.imgt.org/IMGTlect/)], the IMGT Repertoire database (http://www.imgt.org/IMGTrepertoire/), the IMGT/GENE-DB database [described in Giudicelli et al., 2005, Nucleic Acids Res., 2005 Jan. 1; 33 (Database Issue); D256-61 (http://www.imgt.org/IMGT_GENE-DB/GENElect)], and the Kabat database (http://www.kabatdatabase.com). The CDRs contained in the anti-single-chain type IV collagen polypeptide antibody may be isolated by comparison with the CDR sequence information registered in these databases.

The anti-single-chain type IV collagen polypeptide antibody according to the first embodiment preferably contain an H chain containing at least one CDR selected from the amino acid sequences represented by SEQ ID NOs: 5 to 7 and 11 to 13, and an L chain containing at least one CDR selected from the amino acid sequences represented by SEQ ID NOs: 8 to 10 and 14 to 16, more preferably the combination of an H chain containing at least one CDR selected from the amino acid sequences represented by SEQ ID NOs: 5 to 7, and an L chain containing at least one CDR selected from the amino acid sequences represented by SEQ ID NOs: 8 to 10, or the combination of an H chain containing at least one CDR selected from the amino acid sequences represented by SEQ ID NOs: 11 to 13, and an L chain containing at least one CDR selected from the amino acid sequences represented by SEQ ID NOs: 14 to 16.

At least any of the CDR amino acid sequences represented by SEQ ID NOs: 5 to 16 in the anti-single-chain type IV collagen polypeptide antibody according to the first embodiment may be an amino acid sequence derived therefrom by the deletion, substitution, insertion, or addition of one or several amino acids.

The anti-single-chain type IV collagen polypeptide antibody according to the first embodiment is preferably an antibody recognizing an epitope containing the amino acid sequence represented by GIGIPGLRG (SEQ ID NO: 41). In this epitope, the amino acid sequence represented by SEQ ID NO: 41 may be an amino acid sequence derived therefrom by the deletion, substitution, insertion, or addition of one or several amino acids.

In addition to the anti-single-chain type IV collagen polypeptide antibody itself according to the first embodiment, for example, a partial structure of the anti-single-chain type IV collagen polypeptide antibody is also included in the scope of the present invention.

The partial structure is not particularly limited as long as the partial structure is a portion of the anti-single-chain type IV collagen polypeptide antibody specifically recognizing the single-chain type IV collagen polypeptide. The partial structure can be selected appropriately according to the purpose. Examples thereof include partial structures including Fab, F(ab')$_2$, V regions, complementarity determining regions (CDRs), and single chain antibodies (scFvs), which bind to the antigen (single-chain type IV collagen polypeptide).

The anti-single-chain type IV collagen polypeptide antibody according to the second embodiment is not particularly limited as long as it is a monoclonal antibody containing an H chain containing at least one amino acid sequence selected from the amino acid sequences represented by SEQ ID NOs: 5 to 7, and an L chain containing at least one amino acid sequence selected from the amino acid sequences represented by SEQ ID NOs: 8 to 10, or a monoclonal antibody containing an H chain containing at least one amino acid sequence selected from the amino acid sequences represented by SEQ ID NOs: 11 to 13, and an L chain containing at least one amino acid sequence selected from the amino acid sequences represented by SEQ ID NOs: 14 to 16. The anti-single-chain type IV collagen polypeptide antibody according to the second embodiment can be selected appropriately according to the purpose.

The anti-single-chain type IV collagen polypeptide antibody according to the second embodiment also includes, for example, a chimeric antibody, a humanized antibody, a human antibody, and a mouse antibody containing the H chain and the L chain, within the scope of the present invention. Among these antibodies, a humanized antibody or a human antibody is particularly preferred.

At least any of the amino acid sequences represented by SEQ ID NOs: 5 to 16 in the anti-single-chain type IV collagen polypeptide antibody according to the second embodiment may be an amino acid sequence derived therefrom by the deletion, substitution, insertion, or addition of one or several amino acids.

In addition to the anti-single-chain type IV collagen polypeptide antibody itself according to the second embodiment, for example, a partial structure of the anti-single-chain type IV collagen polypeptide antibody is also included in the scope of the present invention.

The partial structure is not particularly limited as long as the partial structure is a portion of the anti-single-chain type IV collagen polypeptide antibody specifically recognizing the single-chain type IV collagen polypeptide. The partial structure can be selected appropriately according to the purpose. Examples thereof include partial structures including Fab, F(ab')$_2$, V regions, CDRs, and single chain antibodies (scFvs), which bind to the antigen (single-chain type IV collagen polypeptide).

The anti-single-chain type IV collagen polypeptide antibody according to the third embodiment is not particularly limited as long as it recognizes an epitope containing the amino acid sequence represented by GIGIPGLRG (SEQ ID NO: 41). The anti-single-chain type IV collagen polypeptide antibody according to the third embodiment can be selected appropriately according to the purpose.

The anti-single-chain type IV collagen polypeptide antibody according to the third embodiment also includes, for example, a chimeric antibody, a humanized antibody, a human antibody, and a mouse antibody recognizing the amino acid sequence represented by SEQ ID NO: 41, within the scope of the present invention. Among these antibodies, a humanized antibody or a human antibody is particularly preferred.

In the epitope, the amino acid sequence represented by SEQ ID NO: 41 may be an amino acid sequence derived therefrom by the deletion, substitution, insertion, or addition of one or several amino acids.

In addition to the anti-single-chain type IV collagen polypeptide antibody itself according to the third embodiment, for example, a partial structure of the anti-single-chain type IV collagen polypeptide antibody is also included in the scope of the present invention.

The partial structure is not particularly limited as long as the partial structure is a portion of the anti-single-chain type IV collagen polypeptide antibody specifically recognizing the single-chain type IV collagen polypeptide. The partial structure can be selected appropriately according to the purpose. Examples thereof include partial structures including Fab, F(ab')$_2$, V regions, CDRs, and single chain antibodies (scFvs), which bind to the antigen (single-chain type IV collagen polypeptide).

In the present invention, the "epitope" refers to a particular site in the protein (antigen) to which the antibody binds. This particular site includes both linear and nonlinear epitopes.

A molecular biological, cell engineering, or biochemical approach known in the art can be used as a method for identifying the epitope.

Hereinafter, the method for identifying the epitope will be shown as an example.

Total RNA is prepared from a human cell line producing the single-chain type IV collagen polypeptide, and the full-length type IV collagen α1 gene (COL4A1, NCBI Gene ID: 1282) is cloned using the total RNA to prepare a COL4A1 expression vector (wild-type). Next, various variant COL4A1 expression vectors (variants) are also prepared with the cloned COL4A1 cDNA as a template. The wild-type or each variant COL4A1 expression vector thus prepared is introduced to an appropriate cultured cell line (e.g., a human cell line) to transiently overexpress the wild-type or variant single-chain type IV collagen polypeptide. The supernatant or extract of the cultured cells thus caused to transiently express the wild-type or variant single-chain type IV collagen polypeptide can be used in Western blotting with the anti-single-chain type IV collagen polypeptide antibody as a primary antibody to identify the epitope in the single-chain type IV collagen polypeptide recognized by the anti-single-chain type IV collagen polypeptide antibody.

In addition to the method, a peptide having a partial sequence of the type IV collagen polypeptide is chemically synthesized, and the epitope in the single-chain type IV collagen polypeptide recognized by the anti-single-chain type IV collagen polypeptide antibody may be identified by dot blot, ELISA, or the like using the peptide.

Alternatively, the epitope in the single-chain type IV collagen polypeptide recognized by the anti-single-chain type IV collagen polypeptide antibody may be identified by the combination of these two types of methods.

Methods for preparing the anti-single-chain type IV collagen polypeptide antibodies of the present invention are not particularly limited and can be selected appropriately according to the purpose from among approaches known in the art. Examples thereof include immunological approaches, phage display method, and ribosome display method. Among these methods, an immunological approach is preferred.

Next, the preparation of the anti-single-chain type IV collagen polypeptide antibody by the immunological approach will be shown as an example.

The antigen used in the immunological approach is not particularly limited and can be selected appropriately according to the purpose. Examples thereof include chemically synthesized antigens, recombinant antigens, and antigens purified from biological samples. These antigens may be used alone or in combination of two or more thereof. Among these antigens, a protein having the full-length amino acid sequence of the single-chain type IV collagen polypeptide is preferably used as the antigen. In the preparation of the anti-single-chain type IV collagen polypeptide antibody, an effective immune-inducing effect may not be expected due to the low molecular weight of the antigen. In such a case, an antigen conjugated with a carrier protein is preferably used.

The carrier protein is not particularly limited and can be selected appropriately according to the purpose. Examples thereof include keyhole light hemocyanin (KLM), bovine serum albumin (BSA), and ovalbumin (OVA). These carrier proteins may be used alone or in combination of two or more thereof.

A method for conjugating the carrier protein with the antigen is not particularly limited and can be selected appropriately according to the purpose. Examples thereof include carbodiimide method, glutaraldehyde method, diazo condensation method, and maleimidobenzoyloxy-succinimide (MBS) method.

Alternatively, an antigen may be expressed as a fusion protein of the single-chain type IV collagen polypeptide (or a portion thereof) with GST, β galactosidase, a maltose-binding protein, a histidine tag, or the like, and used as the antigen. Such a fusion protein can be purified conveniently by a method widely used.

Specific examples of the method for preparing the anti-single-chain type IV collagen polypeptide antibody by the immunological approach include a method involving: sensitizing the desired animal with the antigen; if necessary, repeating immunization by sensitization; collecting blood from the animal after its antibody titer sufficiently rises; and obtaining serum by centrifugation treatment or the like. Antibody-producing cells are extracted from the immunized animal after its antibody titer sufficiently rises.

Next, the obtained antibody-producing cells are fused with a myeloma cell line to obtain hybridomas. Subsequently, these hybridomas are prepared into single clones. Then, a clone producing an antibody having high specificity for the single-chain type IV collagen polypeptide is selected. A culture solution of the selected clone is purified to obtain the antibody of interest.

Alternatively, the hybridomas may be grown into the desired number or more, then intraperitoneally transplanted to an animal (e.g., a mouse), and grown in the ascitic fluid, which can then be purified to obtain the antibody of interest.

The purification of the culture solution or the purification of the ascitic fluid can be carried out preferably by affinity chromatography using protein G, protein A, or the like. Alternatively, such affinity chromatography may be performed with the antigen immobilized on a solid phase. In addition, methods such as ion-exchange chromatography, gel filtration chromatography, ammonium sulfate fractionation, and centrifugation can also be used. These methods are used alone or in arbitrary combination.

Examples of the antibody specifically recognizing the single-chain type IV collagen polypeptide include the anti-single-chain type IV collagen polypeptide antibody of the present invention as well as antibodies known in the art such as JK132 (see Takahashi, S. et al., Connective Tissue (1999) vol. 31; pp. 161-168 and Iwata, M. et al., Journal of Biochemistry (1995) vol. 117 (6); pp. 1298-1304). The anti-single-chain type IV collagen polypeptide antibody is more advantageous than the antibodies known in the art, because the anti-single-chain type IV collagen polypeptide antibody has high affinity for the antigen (single-chain type IV collagen polypeptide).

The hybridoma line of the present invention was designated as Anti NK-Antigen monoclonal antibody #141 line and internationally deposited under Accession No: FERM BP-11300 (receipt date: Oct. 5, 2010) with International Patent Organism Depositary, National Institute of Advanced Industrial Science and Technology (Tsukuba Central 6, 1-1-1 Higashi, Tsukuba, Ibaraki, 305-8566, Japan).

The hybridoma line can produce the anti-single-chain type IV collagen polypeptide antibody.

The pharmaceutical drug of the present invention contains at least the anti-single-chain type IV collagen polypeptide antibody of the present invention and/or a partial structure thereof and further contains, if necessary, additional ingredients. In the present invention, the partial structure preferably contains the CDRs or epitope recognition sites of the single-chain type IV collagen polypeptide, i.e., the antigen-binding sites of the anti-single-chain type IV collagen polypeptide antibody.

The pharmaceutical drug of the present invention is preferably used as the diagnostic, preventive, or therapeutic drug for tumor (e.g., anticancer agent) of the present invention described below.

The pharmaceutical drug also includes a pharmaceutical composition containing the anti-single-chain type IV collagen polypeptide antibody and/or a partial structure thereof. The pharmaceutical composition further contains, in addition to the anti-single-chain type IV collagen polypeptide antibody, a carrier for pharmaceutical use.

The carrier for pharmaceutical use is not particularly limited as long as the carrier is any of physiologically acceptable solvents, dispersion media, coating agents, antibacterial agents, antifungal agents, tonicity agent, absorption-delaying agents, etc., suitable for administration to humans or non-human mammals.

Specific examples of the carrier for pharmaceutical use include water, saline, phosphate-buffered saline, glucose, glycerin, and ethanol used alone or in combination. In many cases, the composition preferably contains a substance serving as a tonicity agent, for example, a saccharide, a polyhydric alcohol (e.g., mannitol or sorbitol), or sodium chloride. The carrier for pharmaceutical use may further contain a trace amount of an auxiliary substance such as a wetting agent or an emulsifier, an antiseptic, or a buffer. These substances are advantageous in enhancing the storage stability or effectiveness of the anti-single-chain type IV collagen polypeptide antibody or the partial structure of the anti-single-chain type IV collagen polypeptide antibody.

The dosage form of the pharmaceutical drug is not particularly limited. The pharmaceutical drug is, for example, in any of liquid, semisolid, and solid dosage forms. Specific examples thereof include solutions (e.g., injectable solutions and insoluble solutions), dispersions, suspensions, tablets, pills, powders, liposomes, and suppositories.

The dosage form is appropriately selected according to an administration route or indications. An injectable dosage form is preferred. Examples of preferable composition of the injectable dosage form include dosage forms of injectable solutions or insoluble solutions and specifically include those suitable for intramuscular injection, preferably subcutaneous injection.

In addition, the pharmaceutical drug can be in any of solution, microemulsion, dispersion, and liposome forms, and other forms suitable for administration without limitations as long as the pharmaceutical drug is sterile and stable under production and storage conditions. The anti-single-chain type IV collagen polypeptide antibody and/or the partial structure thereof is incorporated in a necessary amount of an appropriate solvent, if necessary together with one or the combination of the ingredients listed above. Subsequently, the mixture can be sterilized by filtration to prepare an injectable sterile solution.

In general, the anti-single-chain type IV collagen polypeptide antibody and/or the partial structure thereof is incorporated in a sterile medium containing a basic dispersion medium and necessary additional ingredient(s) listed above to prepare a dispersion. In the case of a sterile powder for preparing the injectable sterile solution, a preferable preparation method involves obtaining, by vacuum drying and freeze drying, a powder of an active ingredient with arbitrary desired additional ingredients from the solution already sterilized by filtration. For example, a particle size necessary for a dispersion can be maintained by use of a coating agent such as lecithin, while the appropriate flowability of a solution can be maintained by use of a surfactant. Absorption-delaying agents such as monostearate and gelatin can be contained in the composition and thereby achieve the sustained absorption of the injectable composition.

The administration route of the pharmaceutical drug is preferably a parenteral route including intravenous, subcutaneous, intraperitoneal, and intramuscular routes. Subcutaneous administration is preferred. In addition to injection, implants and transdermal patches may be used, or an active compound may be prepared using a carrier that protects the anti-single-chain type IV collagen polypeptide antibody and/or the partial structure thereof against rapid release, such as a controlled-release preparation (see Sustained and Controlled Release Drug Delivery Systems, J. R. Robinson ed., Marcel Dekker, Inc., New York, 1978) including microcapsule delivery systems. A biodegradable or biocompatible polymer can be used, such as ethylene-vinyl acetate, polyethylene glycol (PEG), polyanhydride, polyglycolic acid, collagen, polyorthoester, or polylactic acid.

Alternatively, the pharmaceutical drug may be administered orally. In this case, preferably, the anti-single-chain type IV collagen polypeptide antibody and/or the partial structure thereof are coated with a material preventing the inactivation of the compound, or the anti-single-chain type IV collagen polypeptide antibody and/or the partial structure thereof are administered simultaneously with the material preventing the inactivation.

For example, the pharmaceutical drug may be enclosed in a hard or soft gelatin capsule and/or compressed to prepare a tablet. Alternatively, the pharmaceutical drug may be administered orally together with an inert diluent or an absorbable and edible carrier. In addition, the pharmaceutical drug may be incorporated directly in a diet for a test subject. In relation to oral administration for treatment, the anti-single-chain type IV collagen polypeptide antibody and/or the partial structure thereof may be incorporated with an excipient and then used in a dosage form for ingestion, such as tablets, sublingual tablets, troches, capsules, elixirs, suspensions, syrups, or cachets.

The content of the anti-single-chain type IV collagen polypeptide antibody and/or the partial structure thereof in the pharmaceutical drug is not particularly limited and is appropriately adjusted according to the therapeutic or preventive purpose.

The actual dose thereof is appropriately adjusted according to, for example, the disease state, age, sex, and body weight of an individual. In the present invention, administration for prevention refers to administration for preventing postoperative recurrence or suppressing exacerbation at an initial stage of a disease.

A single dose for administration is not particularly limited and can be selected appropriately according to the purpose. The single dose is usually 0.1 mg/kg to 250 mg/kg, more preferably 0.5 mg/kg to 50 mg/kg, particularly preferably approximately 5 mg/kg. The dose can be adjusted for each administration according to a symptom to be treated. Alternatively, a dose that falls outside this range may be applied in consideration of the symptom, general status, etc. of a patient.

The administration schedule of the pharmaceutical drug may be any of single-dose administration and continuous administration. Also, drug holidays following administration for a given period may be set, and then, administration can be resumed.

The pharmaceutical drug may be used in combination with one or more additional pharmaceutical drugs. The pharmaceutical drugs to be combined therewith are appropriately selected in consideration of symptoms or adverse reaction. In the present invention, such combined use also includes the administration of the pharmaceutical drug of the present invention simultaneously or almost simultaneously with the additional pharmaceutical drugs as well as the formulation of the pharmaceutical drug of the present invention together with the additional pharmaceutical drugs.

The pharmaceutical drugs that can be combined with the pharmaceutical drug of the present invention are appropriately selected according to symptoms. Examples thereof include: pharmaceutical drugs having antitumor activity, for example, platinum-containing drugs such as cisplatin, carboplatin, and oxaliplatin; alkylating agents such as cyclophosphamide and melphalan; metabolic antagonists such as gemcitabine, TS-1,5-fluorouracil, and methotrexate; antitumor antibiotics such as bleomycin, daunomycin, and Adriamycin; alkaloids such as irinotecan, paclitaxel, etoposide, and vincristine; anticancer agents such as hormones; molecular target drugs such as erlotinib, gefitinib, and sorafenib; and antibody drugs such as trastuzumab and bevacizumab.

The dosage form, administration route, dose, and administration schedule of the pharmaceutical drug used as a pharmaceutical drug or a pharmaceutical composition for prevention are the same as in use for treatment.

The pharmaceutical drug of the present invention also includes a kit for treatment. The kit for treatment contains the pharmaceutical drug or the pharmaceutical composition of the present invention and one or more additional pharmaceutical drugs for combined use therewith.

A target by the diagnosis, prevention, or treatment of the present invention is not particularly limited. The diagnosis, prevention, or treatment of the present invention can be applied to every solid cancer such as lung cancer, stomach cancer, liver cancer, colon cancer, kidney cancer, pancreatic cancer, gallbladder cancer, and ovary cancer, and to hematopoietic organ tumor. A patient confirmed to have the expressed single-chain type IV collagen polypeptide can be diagnosed, prevented, or treated by the present invention. In order to carry out the diagnosis, prevention, or treatment of the present invention, any of the anti-single-chain type IV collagen polypeptide antibody of the present invention and/or the partial structure thereof alone, the pharmaceutical drug of the present invention, and the pharmaceutical composition of the present invention can be used. In the case of using the pharmaceutical drug or the pharmaceutical composition of the present invention as a pharmaceutical drug or a pharmaceutical composition for prevention, the pharmaceutical drug or the pharmaceutical composition is effectively used as a preventive agent for metastasis intended for the prevention of metastasis after solid cancer surgery and the prevention of recurrence.

The diagnostic or preventive for tumor, or the anticancer agent of the present invention contains at least the anti-single-chain type IV collagen polypeptide antibody. The diagnostic drug for tumor may be provided in the form of a kit for diagnosis. The kit is also included in the present invention.

The kit for diagnosis of tumor contains at least the anti-single-chain type IV collagen polypeptide antibody and may additionally contain, if necessary, a labeling material or a solid-phase reagent with the anti-single-chain type IV collagen polypeptide antibody or a labeled product thereof immobilized thereon.

The labeled product of the anti-single-chain type IV collagen polypeptide antibody means the anti-single-chain type IV collagen polypeptide antibody labeled with an enzyme, a radioisotope, a fluorescent compound, or chemiluminescent compound. The kit may further contain, in addition to the components described above, other reagents for detection, for example, an enzyme substrate (chromogenic substrate, etc.), an enzyme substrate-dissolving solution, an enzyme reaction stop solution, or a diluent for specimens, in the case of an enzyme-labeled product.

Tumor detection using the anti-single-chain type IV collagen polypeptide antibody can be performed by: binding a specimen (such as a biological sample collected from a test subject, for example, blood) to the anti-single-chain type IV collagen polypeptide antibody or the structure thereof through antigen-antibody reaction; and measuring the amount of the antigen (single-chain type IV collagen polypeptide) of interest in the sample on the basis of the amount of the bound antibody.

The amount of the antigen can be detected according to immunological assay known in the art. For example, immunoprecipitation, immunoagglutination, labeled immunoassay, immunonephelometry, Western blotting, and flow cytometry can be used.

In the labeled immunoassay, the signal of the anti-single-chain type IV collagen polypeptide antibody is indicated by the amount of the label detected directly using the labeled antibody or may be indicated by a relative value using a standard solution of an antibody having a known concentration or a known antibody titer. Specifically, the standard solution and the specimen are assayed using a meter, and the signal of the anti-single-chain type IV collagen polypeptide antibody in the sample can be indicated by a value relative to the value of the standard solution. Examples of the labeled immunoassay include ELISA, EIA, RIA, fluorescence immunoassay (FIA), and luminescence immunoassay. Among these methods, ELISA is preferred in terms of convenience and high sensitivity.

On the basis of the tumor detection using the anti-single-chain type IV collagen polypeptide antibody, the state of the tumor can be evaluated or diagnosed with the detection results obtained by the detection method as an index. For example, provided that a sample having detection results exceeding the predetermined reference value is tumor-positive while a sample having detection results equal to or lower than the predetermined reference value is tumor-negative, the positive sample can be determined to have the possibility of being already affected by any tumor and evaluated for the state of its tumor.

The state of the tumor means the presence or absence of developed tumor or the degree of progression thereof. Examples thereof include the presence or absence of developed tumor, the degree of progression thereof, the degree of malignancy thereof, the presence or absence of metastasis, and the presence or absence of recurrence. For the evaluation, one of these states of the tumor may be selected, or the appropriate combination of two or more thereof may be selected.

In order to evaluate the presence or absence of the tumor, the presence or absence of developed tumor is confirmed with the predetermined reference value as a threshold, on the basis of the detection results. The degree of malignancy of the tumor serves as an index representing the extent to which cancer has progressed. The degree of malignancy can be evaluated by stage classification on the basis of the detection results or may be evaluated by classification into early cancer and advanced cancer. For example, the tumor may be evaluated as early cancer or advanced cancer with the detection results as an index. The metastasis of the tumor is evaluated, with the detection results as an index, on the basis of whether or not a neoplasm appears at a site distant from the position of the primary tumor. The recurrence of the tumor is evaluated on the basis of whether or not detection results obtained after intermission or remission exceeds the predetermined reference value again.

EXAMPLES

Hereinafter, the present invention will be described more specifically with reference to Examples. However, these Examples are provided for illustrative purposes and do not limit the present invention by any means. Commercially available reagents described in Examples were used according to instruction manuals provided by manufacturers, unless otherwise specified.

Example 1

A human liver cancer cell line HLF (obtained from RIKEN CELL BANK) and a human kidney cancer cell line UO31 (manufactured by National Cancer Institute) were separately cultured under conditions of 37° C. and 5% $CO_2$ using an RPMI1640 medium (manufactured by Mediatech Inc.) supplemented with 10% by volume of fetal bovine serum (manufactured by Tissue Culture Biologicals Inc.). When the cells became confluent, the medium was replaced by a serum-free RPMI1640 medium, followed by culture for 48 hours. Then, the culture supernatant was recovered. To this culture supernatant, a 4× buffer solution for electrophoresis samples [8 (mass/volume) % sodium dodecyl sulfate (SDS), 40 (volume) % glycerol, 20 (volume) % 2-mercaptoethanol, 0.008 (mass/volume) % bromphenol blue, 0.25 M Tris-HCl, pH 6.8 (in Examples below, the buffer solution for electrophoresis samples used had the same composition as this composition)] was added in an amount of 1/4 (volume ratio), and the mixture was heated at 90° C. for 5 minutes to prepare samples [reduction treatment (+)]. Also, the same operation as above was conducted except that the 4× buffer solution for electrophoresis samples was free from 2-mercaptoethanol to prepare samples [reduction treatment (−)].

These samples were subjected to 4.5 (mass/volume) % SDS-polyacrylamide gel electrophoresis using XV PANTERA MP System (manufactured by D.R.C. Co., Ltd.) and transfer to polyvinylidene difluoride (PVDF) membranes. Two such PVDF membranes were prepared per sample, each blocked with 5 (mass/volume) % skimmed milk, and then incubated with an antibody solution of JK132 (anti-human type IV collagen α1 polypeptide mouse monoclonal antibody, provided by Professor Yasutada Imamura, Animal Cell Technology Laboratory, Department of Applied Chemistry, Faculty of Engineering, Kogakuin University; in the description below, the same holds true for this antibody) or Ab6586 (anti-type IV collagen rabbit polyclonal antibody, manufactured by Abcam plc.; in the description below, the same holds true for this antibody) at room temperature for 1 hour. After 10-minute washing with TBS-Tween 20 (20 mM Tris-HCl (pH 7.4), 150 mM NaCl, 0.1 (volume) % Tween 20) three times, the membranes were incubated with an antibody solution of an HRP-labeled anti-mouse IgG antibody (manufactured by GE Healthcare Japan Corp.) as a secondary antibody at room temperature for 1 hour. After 10-minute washing with TBS-Tween 20 three times, the membranes were reacted with ECL plus (manufactured by GE Healthcare Japan Corp.) to emit chemiluminescence, which was in turn exposed to X-ray films.

The results are shown in FIG. 1. The antibodies Ab6586 and JK132 detected substantially the same band patterns having one band or two bands differing in mobility. From the unreduced samples [reduction treatment (−)], two proteins were detected: (1) SDS-treated type IV collagen (indicated by "triple-chain COL4" in FIG. 1) that had small mobility and maintained its intermolecular disulfide bonds, and (2) approximately 180-kDa single-chain type IV collagen polypeptide (indicated by "single-chain COL4" in FIG. 1) that had large mobility and originally lacked an intermolecular disulfide bond. From the reduced samples [reduction treatment (+)], only bands with the same mobility as that of the single-chain type IV collagen polypeptide (2) that lacked an intermolecular disulfide bond were detected. The bands of the reduced samples [reduction treatment (+)] include: single chains resulting from the cleavage of the intermolecular disulfide bonds in the SDS-treated type IV collagen (1) that maintained its intermolecular disulfide bonds; and the single-chain type IV collagen polypeptide (2) that lacked an intermolecular disulfide bond. Thus, these cancer cell lines were shown to express the single-chain type IV collagen polypeptide having no intermolecular disulfide bond.

Example 2

A human lung cancer Lu65A (obtained from JCRB: Japanese Collection of Research Bioresources) tumor mass subcutaneously implanted in a nude rat (F344/N-rnu/rnu, 7 weeks old, manufactured by CLEA Japan, Inc.) was cut into a block of approximately 3 mm square and subcutaneously transplanted to the dorsal portion of a nude rat using a trocar. When the tumor volume reached approximately 200 $mm^3$ or larger, cancer tissues were collected. The tissues were homogenized by the addition of a tissue extraction buffer solution (pH 7.4, 0.1 M NaCl/PBS, 5 mM EDTA, protease inhibitor cocktail (manufactured by F. Hoffmann-La Roche Ltd.), 1 mM PMSF) in an amount of 4 times the wet weight. Then, the homogenate was centrifuged at 12,000 rpm for 5 minutes, and the centrifugation supernatant was recovered. To this supernatant, a 4× buffer solution for electrophoresis samples was added in an amount of 1/4 (volume ratio), and the mixture was heated at 90° C. for 5 minutes to prepare samples [reduction treatment (+)]. Also, the same operation as above was conducted except that the 4× buffer solution for electrophoresis samples was free from 2-mercaptoethanol to prepare samples [reduction treatment (−)].

These samples were subjected to 4.5 (mass/volume) % SDS-polyacrylamide gel electrophoresis using XV PANTERA MP System (manufactured by D.R.C. Co., Ltd.) and transfer to PVDF membranes. Two such PVDF membranes were prepared per sample, each blocked with 5 (mass/volume) % skimmed milk, and then incubated with an antibody solution of JK132 or Ab6586 at room temperature for 1 hour. After 10-minute washing with TBS-Tween 20 three times, the membranes were incubated with an HRP-labeled anti-mouse IgG antibody or anti-rabbit IgG antibody (manufactured by GE Healthcare Japan Corp.) as a secondary antibody at room temperature for 1 hour. After 10-minute washing with TBS-Tween 20 three times, the membranes were reacted with ECL to emit chemiluminescence, which was in turn exposed to X-ray films.

Figure 2:
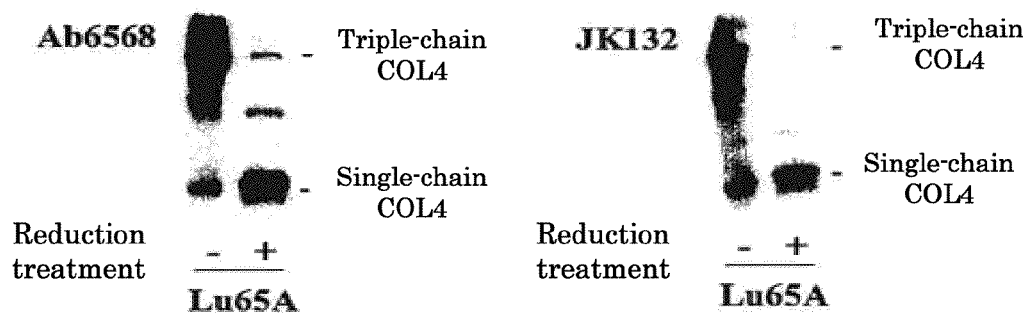
FIG. 2 is a diagram showing one example of the expression of the single-chain type IV collagen polypeptide in the cancer tissue of cancer-bearing (human lung cancer Lu65A) nude rat. The term "triple-chain COL4" represents SDS-denatured type IV collagen that maintains its intermolecular disulfide bonds among the three chains. The term "single-chain COL4" represents the single-chain type IV collagen polypeptide. The mark "−" for reduction treatment represents that a buffer solution for electrophoresis samples is free from 2-mercaptoethanol. The mark "+" for reduction treatment represents that a buffer solution for electrophoresis samples contains 2-mercaptoethanol.

The results are shown in FIG. 2. The antibodies JK132 and Ab6586 detected the band of the single-chain type IV collagen polypeptide (indicated by "single-chain COL4" in FIG. 2) having no intermolecular disulfide bond, from the unreduced samples [reduction treatment (−)]. Thus, the tumor tissues of human lung cancer Lu65A were shown to express the single-chain type IV collagen polypeptide. Since the JK132 antibody reacts with the human single-chain type IV collagen α1 polypeptide but does not react with the mouse single-chain type IV collagen polypeptide, the tumor tissues (human tumor tissues subcutaneously transplanted in the nude rat) of human lung cancer Lu65A were shown to express the human single-chain type IV collagen polypeptide derived from the Lu65A cells.

Example 3

The expression of the single-chain type IV collagen polypeptide in each human cancer cell line was confirmed in the same way as in Example 1 except that the human liver cancer cell line HLF and the human kidney cancer cell line UO31 of Example 1 were changed to human cancer cell lines [Lu65A (obtained from JCRB: Japanese Collection of Research Bioresources), NCI-H460 (manufactured by National Cancer Institute), NCI-H226 (manufactured by National Cancer Institute), MDA-MB-157 (obtained from ATCC: American Type Culture Collection), A498 (obtained from ATCC), Panc-1 (obtained from Cell Resource Center for Biomedical Research, Institute of Development, Aging and Cancer, Tohoku University), OVCAR3 (obtained from Cell Resource Center for Biomedical Research, Institute of Development, Aging and Cancer, Tohoku University), and HT1080 (manufactured by Dainippon Sumitomo Pharma Co., Ltd.)].

Also, the expression of the single-chain type IV collagen polypeptide in human tumor tissues subcutaneously transplanted in nude rats was confirmed in the same way as in Example 2 except that the human lung cancer Lu65A of Example 2 was changed to HLF (obtained from RIKEN CELL BANK).

In addition, human clinical lung cancer tissues (manufactured by Asterand plc., Sample IDs: 110443A1, 112523A1, 107811A1, 111540B1, 112294A1, and 111541A1) or human clinical normal lung tissues (manufactured by Asterand plc., Sample IDs: 98859B2, 112279B1, and 112301B1) obtained from lung cancer patients were separately homogenized by the addition of a tissue extraction buffer solution (pH 7.4, 0.1 M NaCl/PBS, 5 mM EDTA, protease inhibitor cocktail (manufactured by F. Hoffmann-La Roche Ltd.), 1 mM PMSF) in an amount of 4 times the wet weight. Then, the homogenate was centrifuged at 12,000 rpm for 5 minutes, and the centrifugation supernatant was recovered. To this supernatant, the same 4× buffer solution for electrophoresis samples as above except for 2-mercaptoethanol was added in an amount of 1/4 (volume ratio), and the mixture was heated at 90° C. for 5 minutes to prepare samples [reduction treatment (−)].

For the expression of the single-chain type IV collagen polypeptide in the human clinical lung cancer tissues and the human clinical normal lung tissues obtained from lung cancer patients, an anti-β-actin antibody (manufactured by Sigma-Aldrich Corp.) was used in order to examine the amount of β-actin as an internal standard.

Note that, the cancer tissues and the normal lung tissues as the human clinical tissues were pathologically diagnosed by specialists.

Figure 3:
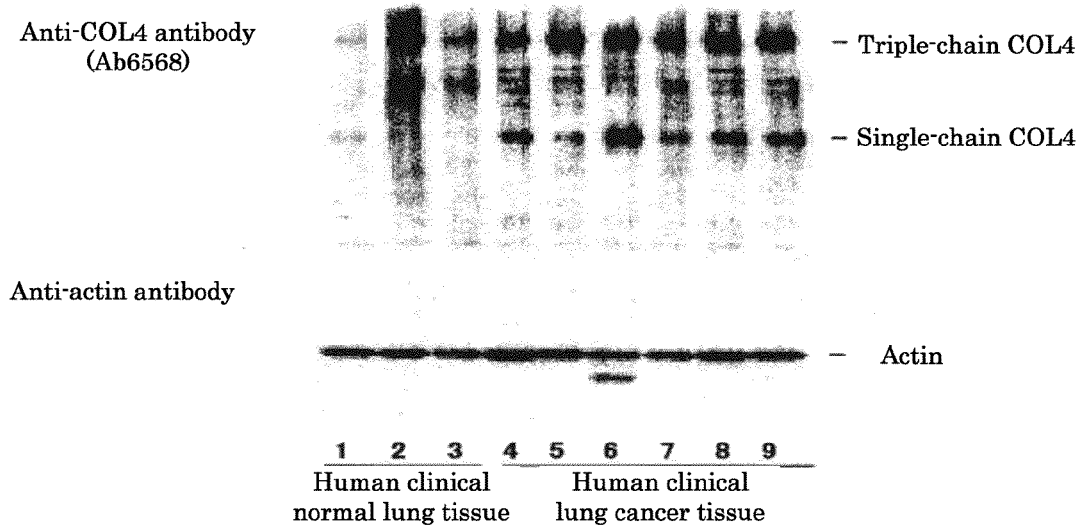
FIG. 3 is a diagram showing results of comparing the expression level of the single-chain type IV collagen polypeptide between human clinical lung cancer tissues and human clinical normal lung tissues obtained from lung cancer patients. The term "triple-chain COL4" represents SDS-denatured type IV collagen that maintains its intermolecular disulfide bonds among the three chains. The term "single-chain COL4" represents the single-chain type IV collagen polypeptide.

The results of the human cancer cell lines (in vitro) confirmed to express the single-chain type IV collagen polypeptide in the same way as in Example 1 and the human tumor tissues (in vivo; subcutaneously transplanted in nude rats) confirmed to express the single-chain type IV collagen polypeptide in the same way as in Example 2 are shown, together with the results of Examples 1 and 2, in Table 1. Also, the results of the human clinical lung cancer tissues and the human clinical normal lung tissues are shown in FIG. 3.

As shown in Table 1, the expression of the single-chain type IV collagen polypeptide was confirmed in these 10 types of human cancer cell lines and 2 types of human tumor tissues subcutaneously transplanted in nude rats. As shown in FIG. 3, the high expression of the single-chain type IV collagen polypeptide was confirmed in all the 6 cases of human clinical lung cancer tissues. By contrast, the expression of the single-chain type IV collagen polypeptide was observed only slightly in the human clinical normal lung tissues obtained from lung cancer patients.

TABLE 1

|  | (In vitro) | (In vivo) |
| --- | --- | --- |
| Lung cancer | Lu65A | Lu65A |
|  | NCI-H460 |  |
|  | NCI-H226 |  |
| Breast cancer | MDA-MB-157 |  |
| Liver cancer | HLF | HLF |
| Kidney cancer | UO31 |  |
|  | A498 |  |
| Pancreatic cancer | Panc-1 |  |
| Ovary cancer | OVCAR3 |  |
| Fibrosarcoma | HT1080 |  |

The results described above demonstrated that the single-chain type IV collagen polypeptide is expressed in the human cancer cell lines and the human tumor tissues subcutaneously transplanted in nude rats, shown in Table 1. Also, the results of FIG. 3 demonstrated that the single-chain type IV collagen polypeptide is highly expressed specifically in tumor tissues.

Example 4

Preparation of Single-Chain Type IV Collagen α1 Polypeptide

—Cell and Cell Culture—

A human liver cancer cell line HLF (RIKEN CELL BANK) was cultured under conditions of 37° C. and 5% $CO_2$ using an RPMI1640 medium (manufactured by Mediatech Inc.) supplemented with 10% by volume of fetal bovine serum (manufactured by Tissue Culture Biologicals Inc.), and then maintained. —Preparation of Single-Chain Type IV Collagen α1 Polypeptide—

The single-chain type IV collagen α1 polypeptide was immunoaffinity-purified from a medium of human liver cancer HLF cells cultured for 7 days in a serum-free RPMI1640 medium (manufactured by Mediatech Inc.), with reference to the method of Takahashi, S. et al. (Takahashi, S. et al., "Connective Tissue" (1999) vol. 31; pp. 161-168).

In brief, first, 4.2 mg of JK132 antibodies were immobilized on HiTrap NHS-activated HP column (manufactured by GE Healthcare Japan Corp.) to prepare a JK132 affinity column. The JK132 affinity column was washed with 0.2 M glycin-HCl (pH 2.5).

Figure 4:
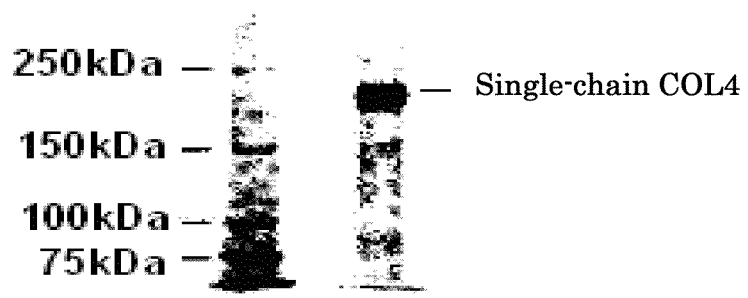
FIG. 4 is a diagram showing one example of a purified product of a single-chain type IV collagen polypeptide produced by a human liver cancer cell line HLF. The term "MW" represents a molecular weight marker.

450 ml of the culture supernatant was applied to 1 ml of the JK132 affinity column. After washing with phosphate-buffered saline, fractions collected with 0.2 M glycine-HCl (pH 2.5) were analyzed by SDS-PAGE and Western blot. The obtained eluted fractions were dialyzed, then freeze-dried, and stored at −80° C. Results of 4.5 (mass/volume) % polyacrylamide gel electrophoresis and subsequent silver staining (manufactured by Daiichi Pure Chemicals Co., Ltd.) of the purified single-chain type IV collagen α1 polypeptide are shown in FIG. 4. Precision Plus Protein Standard Dual Color available from Bio-Rad Laboratories, Inc. was used as a molecular weight marker (MW).

Example 5

Screening of Monoclonal Antibody (NK46141)

—Immunization—

Each female Balb/c mouse (Japan SLC, Inc.) was immunized by intraperitoneal injection using the single-chain type IV collagen α1 polypeptide (antigen) prepared in Example 4. For initial immunization, 100 μg or 20 μg of the single-chain type IV collagen α1 polypeptide in a complete Freund's adjuvant (manufactured by Difco Laboratories, Inc.) was administered per mouse. For subsequent shots, 20 μg to 50 μg of the single-chain type IV collagen α1 polypeptide in an RIBI adjuvant (manufactured by Corixa Corp.) was administered per mouse. The immunization was performed at 2-week to 3-week intervals. Seven days after the final immunization, the antibody titer of the animal was enhanced by booster with phosphate-buffered saline (PBS) containing 25 μg of the single-chain type IV collagen α1 polypeptide.

—Preparation of Hybridoma—

Three days after the booster, spleen cells were prepared from the immunized animal with a high antibody titer according to a routine method. The spleen cells were fused with P3.X63-Ag8.653 mouse myeloma cells (obtained from ATCC, #CRL-1580) using polyethylene glycol 4000 (manufactured by Sigma-Aldrich Corp.). Hybridoma cells were selected in a HAT medium [prepared by suspending 10% by mass of FBS (HyClone; manufactured by Thermo Fisher Scientific Inc.), 500 μM D(+)-glucose (manufactured by Wako Pure Chemical Industries, Ltd.), 2% by mass of penicillin-streptomycin (manufactured by Invitrogen Corp.), 100 μM hypoxanthine sodium (manufactured by Invitrogen Corp.), 0.1 μM aminopterin (manufactured by Invitrogen Corp.), and 16 μM thymidine (manufactured by Invitrogen Corp.) in RPMI1640 (manufactured by Invitrogen Corp.); in Examples below, the HAT medium had the same composition as this composition] using a microtiter plate (Nunc; manufactured by Thermo Fisher Scientific Inc.) according to the technique of Kohler and Milstein known in the art.

—Antibody Titer Measurement—

For the hybridoma selection, the antibody titer of the immunized animal was measured in serum using ELISA shown below. First, a microtiter plate (Nunc; manufactured by Thermo Fisher Scientific Inc.) was coated with the single-chain type IV collagen α1 polypeptide (antigen). Subsequently, serial dilutions of the serum were added to wells blocked with 1 (mass/volume) % BSA/TBS (20 mM Tris-HCl, 150 mM NaCl, pH 7.5)-0.05 (volume) % Tween 20, and then incubated. The antibody bound with the single-chain type IV collagen α1 polypeptide (antigen) was detected using a peroxidase-conjugated antibody against mouse immunoglobulin.

—Hybridoma Screening by ELISA—

The single-chain type IV collagen α1 polypeptide (antigen) (concentration: 1 μg/ml in a 50 mM carbonate buffer) was immobilized on a 96-well microtiter plate (Nunc; manufactured by Thermo Fisher Scientific Inc.) at room temperature for 2 hours. Subsequently, the plate was washed with TBS/0.05 volume) % Tween 20. Free adsorbing portions on the surface of the plate were blocked at room temperature for 30 minutes using 1 (mass/volume) % BSA/TBS-0.05 (volume) % Tween 20. The plate was washed again with TBS/0.05 (volume) % Tween 20. The hybridoma culture supernatant was added to each well and reacted at room temperature for 1 hour. Then, the plate was washed with TBS/0.05 (volume) % Tween 20. Subsequently, 50 μL/well of a peroxidase-conjugated anti-mouse IgG antibody (BETHYL Laboratories, Inc., #E90-131) diluted in 1 (mass/volume) % BSA/TBS-0.05 (volume) % Tween 20 was added thereto. After incubation at room temperature for 1 hour, the plate was washed with TBS/0.05 (volume) % Tween 20, and 100 μL/well of a substrate solution (citrate buffer (pH 5), 0.05 (mass/volume) % o-phenylenediamine, 0.03% by volume of $H_2O_2$) was added to the wells. 20 minutes to 30 minutes after, the reaction was stopped by the addition of 2 N sulfuric acid, and the absorbance was measured at 490 nm using a spectrophotometer.

The hybridoma line thus obtained was internationally deposited under Anti NK-Antigen monoclonal antibody #141 (hereinafter, also referred to as a "#141 line") with International Patent Organism Depositary, National Institute of Advanced Industrial Science and Technology (receipt date: Oct. 5, 2010).

—Purification of Monoclonal Antibody—

The antibody-producing hybridoma #141 line was cultured under conditions of 37° C. and 5% $CO_2$ using a HAT medium to prepare a culture supernatant. Also, the antibody-producing hybridoma #141 line was intraperitoneally administered to a mouse, and its ascitic fluid was collected 7 days to 10 days after and filtered through a filter to remove insoluble matter.

The antibody-producing hybridoma culture supernatant or the mouse ascitic fluid was applied to a column packed with Protein G-Sepharose 4B (GE Healthcare Japan Corp.) according to a routine method to adsorb antibody components thereon. Then, nonspecific adsorbed matter was removed, and a monoclonal antibody released under acidic conditions was then recovered and used as a purified antibody. The obtained purified antibody was dialyzed against a PBS buffer solution in an amount of 100-fold (volume ratio) for buffer replacement. The present inventors designated this monoclonal antibody as "NK46141".

—Isotyping of Monoclonal Antibody NK46141—

NK46141 was isotyped using sandwich ELISA. An anti-mouse IgG goat polyclonal antibody (manufactured by Dako Japan Inc.) (antibody to be immobilized, diluted 1,000-fold with 50 mM carbonate buffer) was dispensed at a concentration of 50 μl/well to 6 well of a 96-well microtiter plate (Nunc; manufactured by Thermo Fisher Scientific Inc.) and immobilized at room temperature for 2 hours. Subsequently, the wells were washed with TBS/0.05 (volume) % Tween 20. Free adsorbing portions on the surface of the wells were blocked at room temperature for 30 minutes using 1 (mass/volume) % BSA/TBS-0.05 (volume) % Tween 20. The plate was washed again with TBS/0.05 (volume) % Tween 20.

50 μl/well of the culture supernatant of the NK46141-producing hybridoma was added thereto and reacted at room temperature for 1 hour. Then, the wells were washed with TBS/0.05 (volume) % Tween 20. 50 μL each of 6 types of antibodies for detection (HRP-labeled anti-mouse IgG1 goat antibody, HRP-labeled anti-mouse IgG2a goat antibody, HRP-labeled anti-mouse IgG2b goat antibody, HRP-labeled anti-mouse IgG3 goat antibody, HRP-labeled anti-mouse IgA goat antibody, and HRP-labeled anti-mouse IgGM goat antibody; all manufactured by BETHYL Laboratories, Inc.) diluted 1.000-fold with 1 (mass/volume) % BSA/TBS-0.05 (volume) % Tween 20 was added to each well (one type for each well). After incubation at room temperature for 1 hour, the plate was washed with TBS/0.05 (volume) % Tween 20, and 100 μ/well of a substrate solution (citrate buffer (pH 5.0), 0.05 (mass/volume) % o-phenylenediamine, 0.03% by volume of $H_2O_2$) was added to the wells. 20 minutes to 30 minutes after, the reaction was stopped by the addition of 2 N sulfuric acid, and the absorbance was measured at 490 nm using a spectrophotometer.

As a result, the isotype of NK46141 was confirmed to be IgG2b.

—Immunoprecipitation Analysis—

For immunoprecipitation analysis, 0.5 μg of the purified monoclonal antibody (NK46141) was incubated at 4° C. for 30 minutes with rotation, together with 500 μl of a culture supernatant of a single-chain type IV collagen α1 polypeptide-expressing human liver cancer cell line HLF cultured in the same way as in Example 1. The same operation as above was conducted except that a positive control JK132 was used instead of NK46141. The same operation as above was conducted except that an isotype control Mouse IgG2b (Functional Grade, manufactured by Medical & Biological Laboratories Co., Ltd. (MBL), M077-3M2) was used instead of NK46141. Likewise, the same operation as above was conducted except that a negative control PBS was used without containing a primary antibody for immunoprecipitation.

Next, 10 μl of Dynabeads M-280 Sheep anti-Mouse IgG secondary antibody (Dynabeads-conjugated goat anti-mouse IgG, manufactured by VERITAS Corp., #DB11201) was added thereto and incubated at 4° C. for 1 hour with rotation. Also, Dynabeads M-280 Sheep anti-Mouse IgG secondary antibody was added to a culture supernatant of a human liver cancer cell line HLF as a negative control and incubated in the same way as above.

The reaction mixture was left standing on a magnet for 2 minutes, and the supernatant was discarded. The Dynabeads were washed three times with 500 μl of a wash buffer (PBS containing 0.05 (volume) % Tween 20 and 2 mM EDTA). To the Dynabeads, 50 μl of a 1× buffer solution for electrophoresis samples free from 2-mercaptoethanol was added, and the mixture was heated at 90° C. for 5 minutes to prepare a sample. This sample was subjected to SDS-polyacrylamide gel electrophoresis and transfer to PVDF membranes. Then, the PVDF membranes were incubated with Ab6586 and analyzed in the same way as in Example 1.

Figure 5:
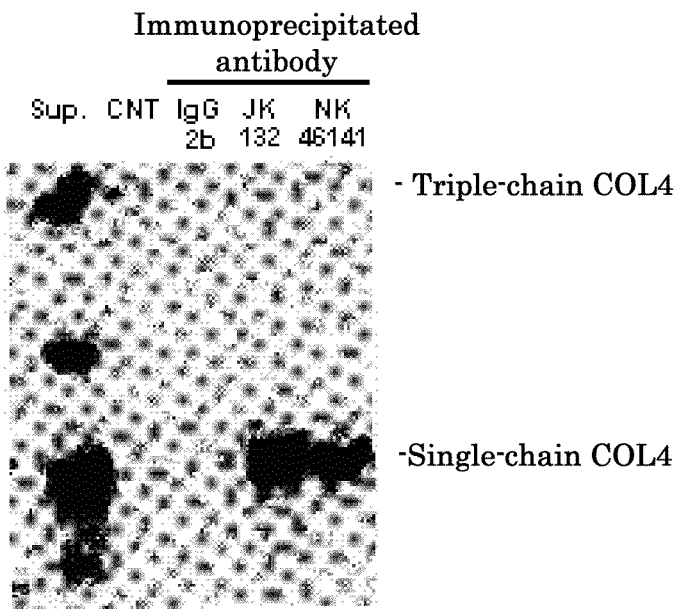
FIG. 5 is a diagram showing, as one example, that an anti-single-chain type IV collagen polypeptide antibody (NK46141) specifically recognizes the single-chain type IV collagen polypeptide. The term "Sup." represents a culture supernatant of human liver cancer cells HLF. The term "CNT" represents PBS used as a negative control without containing a primary antibody for immunoprecipitation. The term "IgG2b" represents a mouse IgG2b isotype control.

The results are shown in FIG. 5. In FIG. 5, the term "Sup." represents the culture supernatant of the human liver cancer cell line HLF before immunoprecipitation, from which several bands were detected with Ab6586. As shown in this diagram, only the single-chain type IV collagen polypeptide was selectively recovered by the immunoprecipitation of this sample with NK46141 or JK132. This immunoprecipitation method demonstrated that NK46141 specifically recognizes the single-chain type IV collagen polypeptide without recognizing type IV collagen.

In this way, the monoclonal antibody NK46141 specifically recognizing the single-chain type IV collagen α1 polypeptide was obtained.

Example 6

Binding Affinity of Monoclonal Antibody NK46141

The dissociation constant of the purified monoclonal antibody NK46141 was determined by ELISA with reference to the method of Djavadi-Ohaniance L. et al. [Djavadi-Ohaniance L., et al., (1996) In Antibody Engineering (Eds.: McCafferty J., et al.), Chapter 4, pp. 77-97., IRL Press, Oxford.].

In brief, Immunoplate (Nunc; manufactured by Thermo Fisher Scientific Inc.) with the single-chain type IV collagen α1 polypeptide (antigen) immobilized thereon in advance was prepared. Meanwhile, JK132 and NK46141 having a constant concentration (0.10 μg/ml) were each incubated with varying concentrations of the antigen for a sufficient time until reaching equilibrium. This incubation solution was added to the ELISA wells to determine the amount of free antibodies. Since the antigen-antibody reaction follows the law of mass action, measured values were applied to formula 1 below. X and Y in formula 2 below were determined, and a graph was drawn to determine the dissociation constant from the slope (1/Kd).

$$x/[\text{Total antibody concentration}] \times 1/[\text{Free antigen}] = (1 - x/[\text{Total antibody concentration}]) \times 1/Kd \quad \text{(Formula 1)}$$

wherein X=x/[Total antibody concentration] and Y=x/([Total antibody concentration]×[Free antigen]

$$Y = (1-X) \times 1/Kd \quad \text{(Formula 2)}$$

The results are shown in Table 2.

TABLE 2

|  | JK132 | NK46141 |
| --- | --- | --- |
| Dissociation constant (M) | $15.3 \times 10^{-8}$ | $3.4 \times 10^{-8}$ |

JK132 and NK46141 had dissociation constants of $15.3 \times 10^{-8}$ M and $3.4 \times 10^{-8}$ M, respectively, demonstrating that NK46141 has higher affinity for the single-chain type IV collagen α1 polypeptide than that of JK132.

Example 7

Analysis of Epitope Site Recognized by Monoclonal Antibody NK46141

Reactivity with the antigen (single-chain type IV collagen α1 polypeptide) was evaluated by sandwich ELISA. The monoclonal antibody NK46141 (antibody to be immobilized, concentration: 5 μg/ml in a 50 mM carbonate buffer) purified in Example 5 was immobilized on a 96-well microtiter plate (Nunc; manufactured by Thermo Fisher Scientific Inc.) at room temperature for 2 hours. Subsequently, the plate was washed with TBS/0.05 (volume) % Tween 20. Free adsorbing portions on the surface of the plate were blocked at room temperature for 30 minutes using 1 (mass/volume) % BSA/TBS-0.05 (volume) % Tween 20. The plate was washed again with TBS/0.05 (volume) % Tween 20. The single-chain type IV collagen α1 polypeptide (1 μg/ml in 1 (mass/volume) % BSA/TBS-0.05 (volume) % Tween 20) was added as an antigen to the wells and reacted at room temperature for 1 hour. Then, the plate was washed with TBS/0.05 (volume) % Tween 20. Subsequently, 50 μL/well of a monoclonal antibody prepared as an HRP-labeled antibody for detection using Peroxidase Labeling Kit-SH (manufactured by Wako Pure Chemical Industries, Ltd.) was added thereto. After incubation at room temperature for 1 hour, the plate was washed with TBS/0.05 (volume) % Tween 20, and 100 μL/well of a substrate solution (citrate buffer (pH 5), 0.05 (mass/volume) % o-phenylenediamine, 0.03% by volume of $H_2O_2$) was added to the wells. 20 minutes to 30 minutes after, the reaction was stopped by the addition of 2 N sulfuric acid, and the absorbance was measured at 490 nm using a spectrophotometer. The results are shown in Table 3.

TABLE 3

|  | HRP-labeled JK132 | HRP-labeled NK46141 |
| --- | --- | --- |
| Immobilized JK132 | 0.273 | 3.354 |
| Immobilized NK46141 | 3.284 | 0.209 |

As a result of this test, the absorbance values obtained with JK132 as the immobilized antibody were 0.273 and 3.354 for the HRP-labeled JK132 antibody and the HRP-labeled monoclonal antibody NK46141, respectively. By contrast, the absorbance values obtained with NK46141 as the immobilized antibody were 3.284 and 0.209 for the HRP-labeled JK132 antibody and the HRP-labeled NK46141 antibody, respectively, demonstrating that NK46141 and JK132 do not compete against each other for binding to the single-chain type IV collagen α1 peptide. This showed that the epitope recognized by NK46141 is located at a site different from the epitope recognized by JK132, demonstrating that NK46141 and JK132 recognize different epitopes.

The results of these analyses thus demonstrating the difference between the monoclonal antibody NK46141 and JK132 in their binding affinity and recognized epitope sites showed that NK46141 and JK132 are antibodies having different activities.

Example 8

Antitumor Effect on Human Lung Cancer Cell Line Transplanted in Nude Mouse

A human lung cancer cell line Lu65A (obtained from JCRB) was cultured under conditions of 37° C. and 5% $CO_2$ using an RPMI1640 medium (manufactured by Mediatech Inc.) supplemented with 10% by volume of fetal bovine serum (manufactured by Tissue Culture Biologicals Inc.), and then maintained. A Lu65A cell suspension having a concentration of $2 \times 10^6$ cells/0.2 ml was subcutaneously transplanted to the dorsal portion of each nude mouse (Balb/cAJcl-nu/nu, 9 weeks old, manufactured by CLEA Japan, Inc.) using a syringe.

The monoclonal antibody NK46141 was administered a total of five times to the tail vein on the day before the tumor transplantation and 3 days, 7 days, 10 days, and 14 days after the transplantation. NK46141 was diluted with saline (manufactured by Otsuka Pharmaceutical Co., Ltd.) for use. Saline was used in a control group.

The tumor volume was measured 7 days, 10 days, 14 days, 17 days, and 21 days after the Lu65A transplantation. The tumor volume was calculated according to the formula $(L \times W^2)/2$ by measuring the major axis (L mm) and short axis (W mm) of the tumor.

Figure 6:
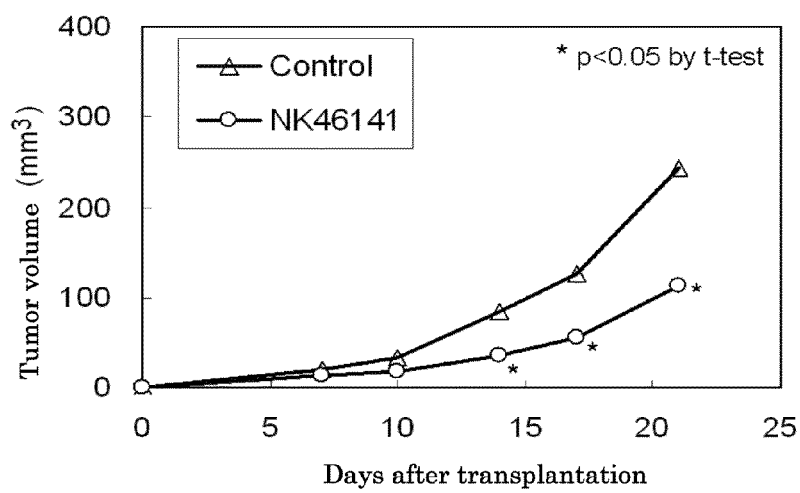
FIG. 6 is a diagram showing, as one example, that the anti-single-chain type IV collagen polypeptide antibody (NK46141) suppresses the growth of tumor in a nude mouse model bearing subcutaneously transplanted human lung cancer Lu65A. The open triangle represents a control group. The open circle represents an administered group that received the anti-single-chain type IV collagen polypeptide antibody (NK46141) of the present invention.

The results are shown in FIG. 6. The NK46141 (30 mg/kg)-administered group of mouse models bearing the subcutaneously transplanted human lung cancer cells Lu65A had a tumor volume significantly (p value <0.05, t-test) smaller than that of the control group that received no NK46141, demonstrating that NK46141 suppresses the growth of tumor tissues.

Example 9

Determination of CDR Sequences of NK46141

Total RNA was obtained from the hybridoma #141 line using RNeasy (manufactured by Qiagen N.V.). From the obtained total RNA, cDNAs encoding the H chain and L chain variable regions of NK46141 were amplified and cloned by 5'-RACE PCR. The gene sequences (SEQ ID NOs: 1 and 2) and amino acid sequences (SEQ ID NOs: 3 and 4) of the NK46141 H chain or L chain variable regions were determined by DNA sequencing and N-terminal amino acid sequence analysis.

NK46141 CDRs were determined by the comparison of the amino acid sequence of NK46141 with the CDR amino acid sequences of known antibodies. Specifically, the IMGT Repertoire database (http://www.imgt.org/IMGTrepertoire/, the IMGT database (IMGT/LIGM-DB database (http://www.imgt.org/IMGTlect/), and the Kabat database (http://www.kabatdatabase.com) were searched for the gene of a known antibody having high homology to NK46141. The CDRs of NK46141 were determined from CDR amino acid sequence information about the obtained antibody gene.

As a result of analysis based on these two types of IMGT databases, the H chain was determined to have a CDR1 sequence GFTFTDYY (SEQ ID NO: 5), a CDR2 sequence ISEGGSYT (SEQ ID NO: 6), and a CDR3 sequence ASPYYGDGGFAY (SEQ ID NO: 7), while the L chain was determined to have a CDR1 sequence QSIVHSDGNTY (SEQ ID NO: 8), a CDR2 sequence KVS (SEQ ID NO: 9), and a CDR3 sequence FQGSHVPPT (SEQ ID NO: 10).

As a result of analysis based on the Kabat database, the H chain was determined to have a CDR1 sequence DYYMY (SEQ ID NO: 11), a CDR2 sequence TISEGGSYTYYPDSVKG (SEQ ID NO: 12), and a CDR3 sequence PYYGDGGFAY (SEQ ID NO: 13), while the L chain was determined to have a CDR1 sequence RSSQSIVHSDGNTYLE (SEQ ID NO: 14), a CDR2 sequence KVSNRFS (SEQ ID NO: 15), and a CDR3 sequence FQGSHVPPT (SEQ ID NO: 16).

Example 10

Identification of Epitope Sequence Recognized by NK46141

In order to narrow down the epitope site recognized by NK46141, various variant single-chain type IV collagen peptides were prepared by a method shown below.
—Cloning of Wild-Type Type IV Collagen α1 Gene—
Total RNA was obtained using RNeasy (manufactured by Qiagen N.V.) from a human liver cancer cell HLF cell line producing the single-chain type IV collagen peptide. From the obtained total RNA, HLF cell-derived cDNA was prepared using reverse transcriptase (Superscript III, manufactured by Invitrogen Corp.). The wild-type type IV collagen α1 gene (COL4A1, NCBI Gene ID: 1282) was amplified by PCR using the HLF cell-derived cDNA as a template and primer sequences represented by SEQ ID NOs: 17 and 18, followed by cloning. The cloned wild-type COL4A1 was confirmed to have no variation by DNA sequencing.
—Preparation of Wild-Type COL4A1 Expression Vector—
The wild-type COL4A1 was subcloned into pENTR1A (manufactured by Invitrogen Corp.). A wild-type COL4A1 expression vector was prepared using LR Clonase (manufactured by Invitrogen Corp.).
—Preparation of Variant COL4A1 Expression Vector 1—
In order to obtain a variant COL4A1 recombinant protein lacking amino acids at residues 29 to 488 in the single-chain type IV collagen α1 polypeptide, a variant COL4A1 expression vector 1 was prepared by the following method:
In order to delete bases corresponding to the amino acid deletion site from residues 29 to 488 in the single-chain type IV collagen peptide, cDNA was amplified by PCR using the wild-type COL4A1 expression vector as a template and primer sequences represented by SEQ ID NOs: 19 and 20. Subsequently, the variant COL4A1 expression vector 1 was prepared in the same way as in the preparation of the wild-type COL4A1 expression vector except that the wild-type COL4A1 in the preparation of the wild-type COL4A1 expression vector was changed to the PCR product.
—Preparation of Variant COL4A1 Expression Vector 2—
A variant COL4A1 expression vector 2 was prepared in the same way as in the preparation of the variant COL4A1 expression vector 1 except that the primer sequences represented by SEQ ID NOs: 19 and 20 in the preparation of the variant COL4A1 expression vector 1 were changed to primer sequences represented by SEQ ID NOs: 21 and 22.

The variant COL4A1 expression vector 2 is an expression vector containing a gene insert with the deletion of bases corresponding to an amino acid deletion site from residues 29 to 989 in the single-chain type IV collagen peptide.

—Preparation of Variant COL4A1 Expression Vector 3—

A variant COL4A1 expression vector 3 was prepared in the same way as in the preparation of the variant COL4A1 expression vector 1 except that the primer sequences represented by SEQ ID NOs: 19 and 20 in the preparation of the variant COL4A1 expression vector 1 were changed to primer sequences represented by SEQ ID NOs: 23 and 24.

The variant COL4A1 expression vector 3 is an expression vector containing a gene insert with the deletion of bases corresponding to an amino acid deletion site from residues 29 to 1,066 in the single-chain type IV collagen peptide.

Since the prepared wild-type COL4A1 expression vector and variant COL4A1 expression vectors 1 to 3 each contain a COL4A1-derived signal sequence, wild-type or variant single-chain type IV collagen peptides transiently overexpressed by mammalian cells are secreted into a culture supernatant.

Thus, the prepared wild-type COL4A1 expression vector and variant COL4A1 expression vectors 1 to 3 were each introduced to human embryonic kidney cell-derived 293FT cells (manufactured by Invitrogen Corp.) to transiently express wild-type or variant single-chain type IV collagen peptides. Hereinafter, the wild-type recombinant protein having the full-length amino acid sequence of the single-chain type IV collagen peptide, expressed using the wild-type COL4A1 expression vector, is also referred to as "FL"; the variant recombinant protein expressed using the variant COL4A1 expression vector 1 is also referred to as "Δ29-488"; the variant recombinant protein expressed using the variant COL4A1 expression vector 2 is also referred to as "Δ29-989"; and the variant recombinant protein expressed using the variant COL4A1 expression vector 3 is also referred to as "Δ29-1,066".

The prepared wild-type COL4A1 expression vector and variant COL4A1 expression vectors 1 to 3 as well as FL, Δ29-488, Δ29-989, and Δ29-1,066 expressed therefrom are summarized in Table 4 below and FIG. 7A.

Figure 7A:
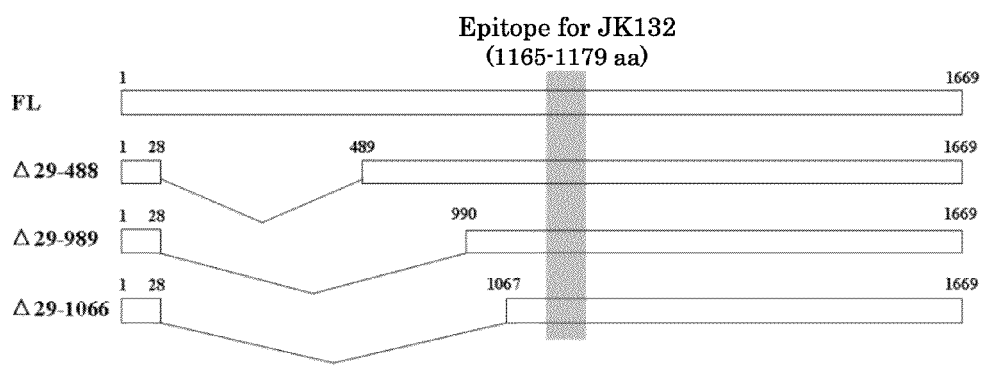
FIG. 7A is a schematic illustrative diagram showing a wild-type recombinant protein (FL) and variant recombinant proteins (Δ29-488, Δ29-989, and Δ29-1,066) expressed using full-length (FL) wild-type type IV collagen α1 gene (COL4A1) and variant COL4A1 expression vectors.

FIG. 7A is a schematic illustrative diagram showing the wild-type single-chain type IV collagen peptide (FL) and these three types of variant single-chain type IV collagen peptides (Δ29-488, Δ29-989, and Δ29-1,066).

TABLE 4

| Expression vector name | Template | Forward primer | Reverse primer | Recombinant protein | Amino acid deletion site |
|---|---|---|---|---|---|
| Wild-type COL4A1 expression vector | HLFcDNA | SEQ ID NO: 17 | SEQ ID NO: 18 | FL | — |
| Variant COL4A1 expression vector 1 | FL | SEQ ID NO: 19 | SEQ ID NO: 20 | Δ29-488 | Residues 29-488 |
| Variant COL4A1 expression vector 2 | FL | SEQ ID NO: 21 | SEQ ID NO: 22 | Δ29-989 | Residues 29-989 |

TABLE 4-continued

| Expression vector name | Template | Forward primer | Reverse primer | Recombinant protein | Amino acid deletion site |
|---|---|---|---|---|---|
| Variant COL4A1 expression vector 3 | FL | SEQ ID NO: 23 | SEQ ID NO: 24 | Δ29-1066 | Residues 29-1066 |

Figure 7B:
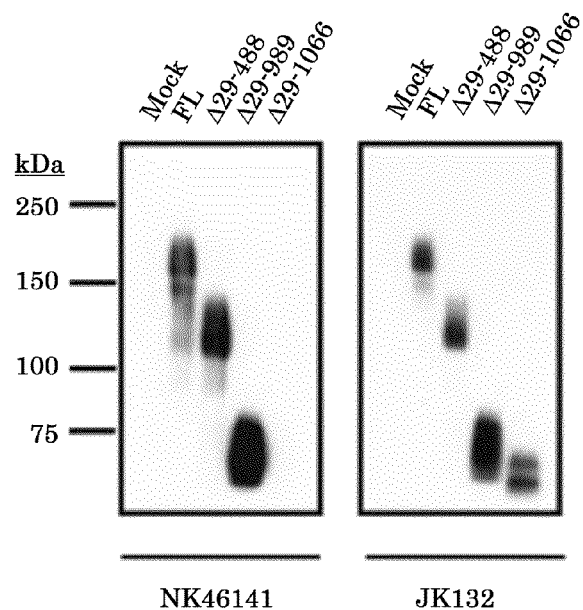
FIG. 7B is a diagram showing results of Western blotting for narrowing down an epitope recognized by the anti-single-chain type IV collagen polypeptide antibody (NK46141). The term "Mock" represents a negative control. JK132 represents a control for gene expression confirmation.

The culture supernatant containing the wild-type single-chain type IV collagen peptide or each of the three types of variant single-chain type IV collagen peptides thus secreted was recovered and subjected to Western blotting with NK46141 as a probe to narrow down the epitope for NK46141. In this regard, only a COL4A1 gene-free vector was introduced to human embryonic kidney cell-derived 293FT cells in the same way as above, and the resulting culture supernatant was used as a negative control (Mock). In addition, the anti-single-chain type IV collagen peptide antibody JK132, which recognizes an epitope different from that for NK46141, was used as a control for gene expression confirmation. The results are shown in FIG. 7B.

As a result, no band was detected for Δ29-1,066, demonstrating that the epitope recognized by NK46141 was located at residues 990 to 1,066 in the amino acid sequence of the single-chain type IV collagen peptide. Note that, the epitope of the type IV collagen α1 polypeptide recognized by JK132 is known to reside at residues 1,165 to 1,179 in the amino acid sequence.

In order to further narrow down the epitope recognized by NK46141, the following variant COL4A1 expression vectors 4 to 6 were prepared.

—Preparation of Variant COL4A1 Expression Vector 4—

A variant COL4A1 expression vector 4 was prepared in the same way as in the preparation of the variant COL4A1 expression vector 1 except that the wild-type COL4A1 expression vector as a template in the preparation of the variant COL4A1 expression vector 1 was changed to the variant COL4A1 expression vector 2 and the primer sequences represented by SEQ ID NOs: 19 and 20 were changed to primer sequences represented by SEQ ID NOs: 25 and 26. Subsequently, a sequence encoding a myc epitope to be tagged at the C-terminus was added to the variant COL4A1 expression vector 4 according to a routine method.

The variant COL4A1 expression vector 4 is an expression vector containing a gene insert with the deletion of bases corresponding to amino acid deletion sites from residues 29 to 989 and from residues 1,067 to 1,669 in the single-chain type IV collagen peptide.

—Preparation of Variant COL4A1 Expression Vector 5—

A variant COL4A1 expression vector 5 was prepared in the same way as in the preparation of the variant COL4A1 expression vector 4 except that the primer sequences represented by SEQ ID NOs: 25 and 26 in the preparation of the variant COL4A1 expression vector 4 were changed to primer sequences represented by SEQ ID NOs: 27 and 28. Subsequently, a sequence encoding a myc epitope to be tagged at the C-terminus was added to the variant COL4A1 expression vector 5 according to a routine method.

The variant COL4A1 expression vector 5 is an expression vector containing a gene insert with the deletion of bases corresponding to amino acid deletion sites from residues 29 to 989 and from residues 1,020 to 1,669 in the single-chain type IV collagen peptide.

—Preparation of Variant COL4A1 Expression Vector 6—

A variant COL4A1 expression vector 6 was prepared in the same way as in the preparation of the variant COL4A1 expression vector 4 except that the variant COL4A1 expression vector 2 as a template in the preparation of the variant COL4A1 expression vector 4 was changed to the variant COL4A1 expression vector 4 and the primer sequences represented by SEQ ID NOs: 25 and 26 were changed to primer sequences represented by SEQ ID NOs: 29 and 30. Subsequently, a sequence encoding a myc epitope to be tagged at the C-terminus was added to the variant COL4A1 expression vector 6 according to a routine method.

The variant COL4A1 expression vector 6 is an expression vector containing a gene insert with the deletion of bases corresponding to amino acid deletion sites from residues 29 to 1,019 and from residues 1,067 to 1,669 in the single-chain type IV collagen peptide.

The prepared variant COL4A1 expression vectors 4 to 6 were each introduced to human embryonic kidney cell-derived 293FT cells (manufactured by Invitrogen Corp.) to transiently express wild-type or variant single-chain type IV collagen peptides into a culture supernatant. Hereinafter, the variant recombinant protein expressed using the variant COL4A1 expression vector 4 is also referred to as "990-1,066 myc"; the variant recombinant protein expressed using the variant COL4A1 expression vector 5 is also referred to as "990-1,019 myc"; and the variant recombinant protein expressed using the variant COL4A1 expression vector 6 is also referred to as "1,020-1,066 myc".

The prepared variant COL4A1 expression vectors 4 to 6 as well as 990-1,066 myc, 990-1,019 myc, and 1,020-1,066 myc expressed therefrom are summarized in Table 5 below and FIG. 9.

FIG. 9 is a schematic illustrative diagram showing these three types of variant single-chain type IV collagen peptides (990-1,066 myc, 990-1,019 myc, and 1,020-1,066 myc).

TABLE 5

| Expression vector name | Template | Forward primer | Reverse primer | Recombinant protein | Amino acid deletion site |
|---|---|---|---|---|---|
| Variant COL4A1 expression vector 4 | Variant COL4A1 expression vector 2 | SEQ ID NO: 25 | SEQ ID NO: 26 | 990-1066 myc | Residues 29-989 Residues 1067-1669 |
| Variant COL4A1 expression vector 5 | Variant COL4A1 expression vector 2 | SEQ ID NO: 27 | SEQ ID NO: 28 | 990-1019 myc | Residues 29-989 Residues 1020-1669 |
| Variant COL4A1 expression vector 6 | Variant COL4A1 expression vector 4 | SEQ ID NO: 29 | SEQ ID NO: 30 | 1020-1066 myc | Residues 29-1019 Residues 1067-1669 |

Figure 8A:
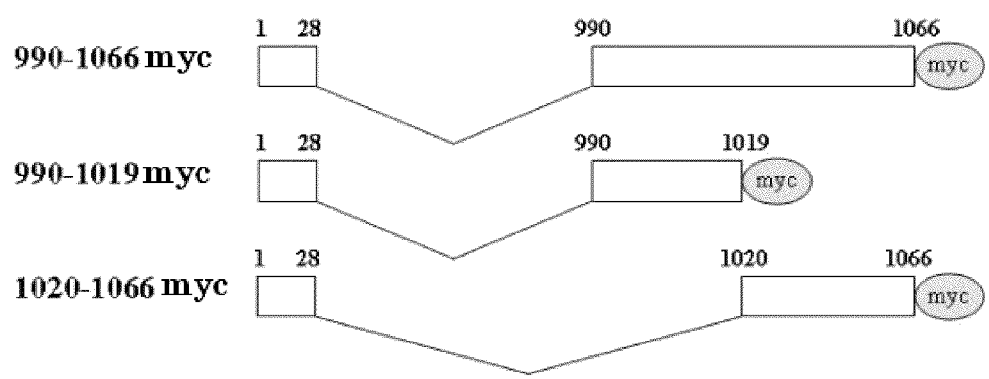
FIG. 8A is a schematic illustrative diagram showing variant recombinant proteins (990-1,066 myc, 990-1,019 myc, and 1,020-1,066 myc) expressed using variant COL4A1 expression vectors. The term "myc" represents an added marker for gene expression confirmation that is recognized by an anti-myc antibody.
Figure 8B:
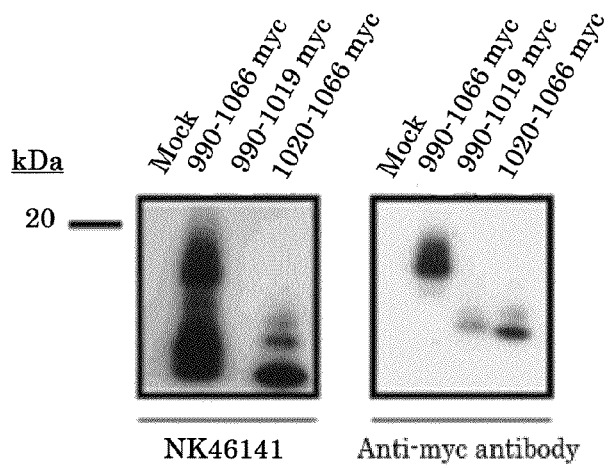
FIG. 8B is a diagram showing results of Western blotting for narrowing down an epitope recognized by the anti-single-chain type IV collagen polypeptide antibody (NK46141). The term "Mock" represents a negative control. The anti-myc antibody represents a control for gene expression confirmation.

The culture supernatant containing each of the three types of variant single-chain type IV collagen peptides thus secreted was recovered and subjected to Western blotting with NK46141 as a probe to narrow down the epitope for NK46141. In this regard, only a COL4A1 gene-free vector was introduced to human embryonic kidney cell-derived 293FT cells in the same way as above, and the resulting culture supernatant was used as a negative control (Mock). In addition, an anti-myc antibody (manufactured by Sigma-Aldrich Corp.) was used as a positive control for confirming the expression of the single-chain type IV collagen peptide. The results are shown in FIG. 8B.

As a result, no band was detected for 990-1,019 myc, demonstrating that the epitope recognized by NK46141 was located at residues 990 to 1,019 in the amino acid sequence of the single-chain type IV collagen peptide.

In order to further narrow down the epitope recognized by NK46141, the following variant COL4A1 expression vectors 7 to 9 were prepared.

—Preparation of Variant COL4A1 Expression Vector 7—

A variant COL4A1 expression vector 7 was prepared in the same way as in the preparation of the variant COL4A1 expression vector 1 except that the primer sequences represented by SEQ ID NOs: 19 and 20 in the preparation of the variant COL4A1 expression vector 1 were changed to primer sequences represented by SEQ ID NOs: 31 and 32.

The variant COL4A1 expression vector 7 is an expression vector containing a gene insert with the deletion of bases corresponding to an amino acid deletion site from residues 1,020 to 1,066 in the single-chain type IV collagen peptide.

—Preparation of Variant COL4A1 Expression Vector 8—

A variant COL4A1 expression vector 8 was prepared in the same way as in the preparation of the variant COL4A1 expression vector 1 except that the primer sequences represented by SEQ ID NOs: 19 and 20 in the preparation of the variant COL4A1 expression vector 1 were changed to primer sequences represented by SEQ ID NOs: 33 and 34.

The variant COL4A1 expression vector 8 is an expression vector containing a gene insert with the deletion of bases corresponding to an amino acid deletion site from residues 1,020 to 1,049 in the single-chain type IV collagen peptide.

—Preparation of Variant COL4A1 Expression Vector 9—

A variant COL4A1 expression vector 9 was prepared in the same way as in the preparation of the variant COL4A1 expression vector 1 except that the primer sequences represented by SEQ ID NOs: 19 and 20 in the preparation of the variant COL4A1 expression vector 1 were changed to primer sequences represented by SEQ ID NOs: 35 and 36.

The variant COL4A1 expression vector 9 is an expression vector containing a gene insert with the deletion of bases corresponding to an amino acid deletion site from residues 1,050 to 1,066 in the single-chain type IV collagen peptide.

The prepared variant COL4A1 expression vectors 7 to 9 were each introduced to human embryonic kidney cell-derived 293FT cells (manufactured by Invitrogen Corp.) to transiently express wild-type or variant single-chain type IV collagen peptides into a culture supernatant. Hereinafter, the variant recombinant protein expressed using the variant COL4A1 expression vector 7 is also referred to as "Δ1,020-1,066"; the variant recombinant protein expressed using the variant COL4A1 expression vector 8 is also referred to as "Δ1,020-1,049"; and the variant recombinant protein expressed using the variant COL4A1 expression vector 9 is also referred to as "Δ1,050-1,066".

The prepared variant COL4A1 expression vectors 7 to 9 as well as Δ1,020-1,066, Δ1,020-1,049, and Δ1,050-1,066 expressed therefrom are summarized, together with the wild-type COL4A1 expression vector, in Table 6 below and FIG. 9A.

Figure 9A:
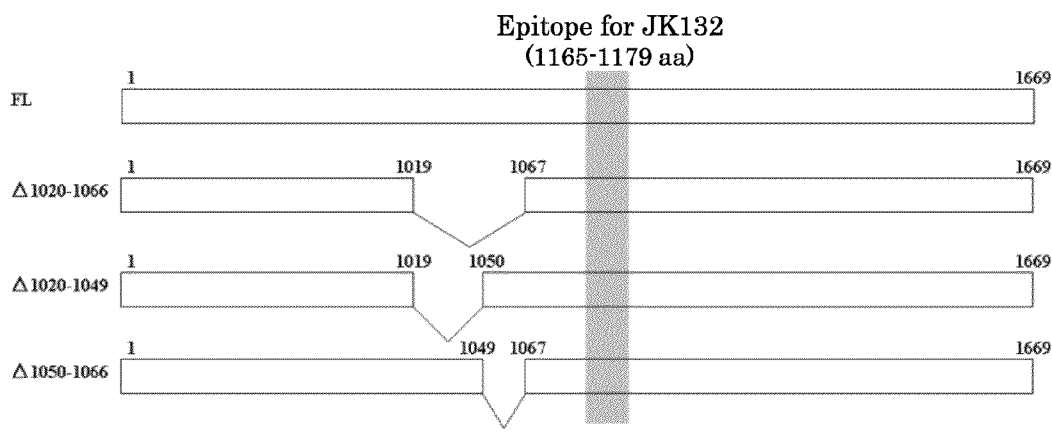
FIG. 9A is a schematic illustrative diagram showing a wild-type recombinant protein (FL) and variant recombinant proteins (Δ1,020-1,066, Δ1,020-1,049, and Δ1,050-1,066) expressed using full-length wild-type COL4A1 and variant COL4A1 expression vectors.

FIG. 9A is a schematic illustrative diagram showing these three types of variant single-chain type IV collagen peptides (Δ1,020-1,066, Δ1,020-1,049, and Δ1,050-1,066).

TABLE 6

| Expression vector name | Template | Forward primer | Reverse primer | Recombinant protein | Amino acid deletion site |
|---|---|---|---|---|---|
| Wild-type COL4A1 expression vector | HLFcDNA | SEQ ID NO: 17 | SEQ ID NO: 18 | FL | — |
| Variant COL4A1 expression vector 7 | FL | SEQ ID NO: 31 | SEQ ID NO: 32 | Δ1020-1066 | Residues 1020-1066 |
| Variant COL4A1 expression vector 8 | FL | SEQ ID NO: 33 | SEQ ID NO: 34 | Δ1020-1049 | Residues 1020-1049 |
| Variant COL4A1 expression vector 9 | FL | SEQ ID NO: 35 | SEQ ID NO: 36 | Δ1050-1066 | Residues 1050-1066 |

Figure 9B:
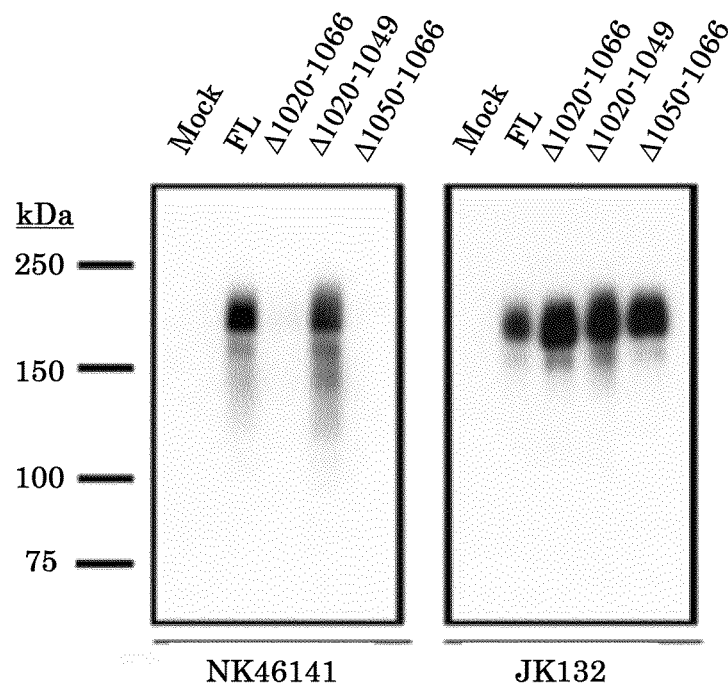
FIG. 9B is a diagram showing results of Western blotting for narrowing down an epitope recognized by NK46141. The term "Mock" represents a negative control. JK132 represents a control for gene expression confirmation.

The culture supernatant containing each of the three types of variant single-chain type IV collagen peptides thus secreted was recovered and subjected to Western blotting with NK46141 as a probe to narrow down the epitope for NK46141. In this regard, only a COL4A1 gene-free vector was introduced to human embryonic kidney cell-derived 293FT cells in the same way as above, and the resulting culture supernatant was used as a negative control (Mock). In addition, the anti-single-chain type IV collagen peptide antibody JK132, which recognizes an epitope different from that for NK46141, was used as a control for gene expression confirmation. The results are shown in FIG. 9B.

As a result, no band was detected for Δ1,020-1,066 or Δ1,050-1,066, demonstrating that the epitope recognized by NK46141 was located at residues 1,050 to 1,066 in the amino acid sequence of the single-chain type IV collagen peptide.

The primer sequences used in the preparation of the wild-type COL4A1 expression vector and the variant COL4A1 expression vectors 1 to 9 in Example 10 are summarized below.

Figure 10:
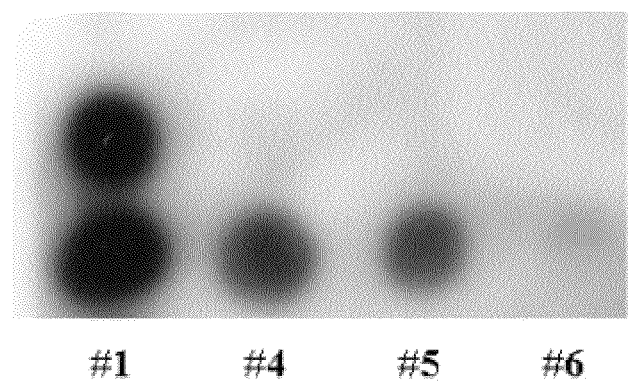
FIG. 10 is a diagram showing results of dot blot for narrowing down an epitope recognized by NK46141. #1: peptide sequence represented by SEQ ID NO: 37. #2: peptide sequence represented by SEQ ID NO: 38. #3: peptide sequence represented by SEQ ID NO: 39. #4: peptide sequence represented by SEQ ID NO: 40. #5: peptide sequence represented by SEQ ID NO: 41. #6: peptide sequence represented by SEQ ID NO: 42.

In order to further determine the epitope recognized by NK46141, the peptide sequences represented by SEQ ID NOs: 37 to 42 shown below were chemically synthesized and used in dot blot with NK46141 as a probe. In FIG. 10, #1 represents the peptide sequence represented by SEQ ID NO: 37; #2 represents the peptide sequence represented by SEQ ID NO: 38; #3 represents the peptide sequence represented by SEQ ID NO: 39; #4 represents the peptide sequence represented by SEQ ID NO: 40; #5 represents the peptide sequence represented by SEQ ID NO: 41; and #6 represents the peptide sequence represented by SEQ ID NO: 42.

As a result, the epitope recognized by NK46141 was shown to be the peptide represented by the amino acid sequence "GIGIPGLRG" (SEQ ID NO: 41) located at residues 1,056 to 1,064 in the amino acid sequence of the type IV collagen α1 polypeptide (#5 of FIG. 10).

|  | Sequence |
|---|---|
| SEQ ID NO: 37 (#1) | GIGIPGLRGEK |
| SEQ ID NO: 38 (#2) | IGIPGLRGEK |
| SEQ ID NO: 39 (#3) | GIPGLRGEK |
| SEQ ID NO: 40 (#4) | GIGIPGLRGE |
| SEQ ID NO: 41 (#5) | GIGIPGLRG |
| SEQ ID NO: 42 (#6) | GIGIPGLR |

The present invention has been described above with reference to Examples. However, these Examples are provided merely for illustrative purposes. It should be understood by those skilled in the art that various changes or modifications can be made therein and such changes or modifications fall within the scope of the present invention.

Accession Number

FERM BP-11300

INDUSTRIAL APPLICABILITY

As described above, the antibody of the present invention targeting the single-chain type IV collagen polypeptide spe

```
                        Forward primer

5'-GTCGACGCCACCATGGGGCCCCGGCTCAGCGTCTGGCTGCTG-3'  SEQ ID NO: 17
5'-GGTTTCCCAGGGCAGCCAGGGGCCAAGGGCGACAGA-3'        SEQ ID NO: 19
5'-GGACCTAAAGGTGATCCAGGTATAAGTGGA-3'              SEQ ID NO: 21
5'-GGAGATCAAGGGATAGCGGGTTTCCCAGGAAGCCCT-3'        SEQ ID NO: 23
5'-GTCGACGCCACCATGGGGCCCCGGCTCAGCGTCTGGCTGCTG-3'  SEQ ID NO: 25
5'-GTCGACGCCACCATGGGGCCCCGGCTCAGCGTCTGGCTGCTG-3'  SEQ ID NO: 27
5'-GGAACACCTGGAGAGAAAGGTGTGCCTGGC-3'              SEQ ID NO: 29
5'-GGAGATCAAGGGATAGCGGGTTTCCCAGGA-3'              SEQ ID NO: 31
5'-GGGCAGGCAGGCCCACCTGGCATAGGCATC-3'              SEQ ID NO: 33
5'-GGAGATCAAGGGATAGCGGGTTTCCCAGGA-3'              SEQ ID NO: 35

Reverse primer

5'-GCGGCCGCTTATGTTCTTCTCATACAGACTTGGCAGCG-3'      SEQ ID NO: 18
5'-CTTCGCAGCGGCCCGGCTGTGCTCCTCGTGGAGCAG-3'        SEQ ID NO: 20
5'-CTTCGCAGCGGCCCGGCTGTGCTCCTCGTGGAGCAG-3'        SEQ ID NO: 22
5'-CTTCGCAGCGGCCCGGCTGTGCTCCTCGTGGAGCAG-3'        SEQ ID NO: 24
5'-GCGGCCGCGACTTTTCACCTCGCAGCCCTGGGATGCCTAT-3'    SEQ ID NO: 26
5'-TGGCAAGCCCATTCCACCAACAGATCCTTT-3'              SEQ ID NO: 28
5'-CTTCGCAGCGGCCCGGCTGTGCTCCTCGTGGAGCAG-3'        SEQ ID NO: 30
5'-TGGCAAGCCCATTCCACCAACAGATCCTTT-3'              SEQ ID NO: 32
5'-TGGCAAGCCCATTCCACCAACAGATCCTTT-3'              SEQ ID NO: 34
5'-TTTCTCTCCTTTTGCACCTTTGTCTCCAGG-3'              SEQ ID NO: 36
``` cifically expressed in tumor tissues is useful as a pharmaceutical drug or a diagnostic drug that does not act on normal tissues, normal organs, or normal cells, or as a kit for treatment or diagnosis of tumor.

What is claimed is:

1. A hybridoma line, wherein the hybridoma line is Anti NK-Antigen monoclonal antibody #141, having Accession No: FERM BP-11300.

2. A monoclonal antibody comprising:
a heavy chain variable region ($V_H$), and a light chain variable region ($V_L$), wherein
(a) the heavy chain variable region comprises three complementarity determining regions (CDRs), $V_H$ CDR1, $V_H$ CDR2 and $V_H$ CDR3, and
wherein $V_H$ CDR1 comprises the amino acid sequence as set forth in SEQ ID NO: 5, $V_H$ CDR2 comprises the amino acid sequence as set forth in SEQ ID NO: 6 and $V_H$ CDR3 comprises the amino acid sequence as set forth in SEQ ID NO: 7; and
(b) the light chain variable region comprises three complementarity determining regions (CDRs), $V_L$ CDR1, $V_L$ CDR2 and $V_L$ CDR3, and
wherein $V_L$ CDR1 comprises the amino acid sequence as set forth in SEQ ID NO: 8, $V_L$ CDR2 comprises the amino acid sequence as set forth in SEQ ID NO: 9 and $V_L$ CDR3 comprises the amino acid sequence as set forth in SEQ ID NO: 10, and
wherein the monoclonal antibody specifically binds to a single-chain type IV collagen polypeptide.

3. A monoclonal antibody comprising:
a heavy chain variable region ($V_H$), and a light chain variable region ($V_L$), wherein
(a) the heavy chain variable region comprises three complementarity determining regions (CDRs), $V_H$ CDR1, $V_H$ CDR2 and $V_H$ CDR3, and
wherein $V_H$ CDR1 comprises the amino acid sequence as set forth in SEQ ID NO: 11, $V_H$ CDR2 comprises the amino acid sequence as set forth in SEQ ID NO: 12 and $V_H$ CDR3 comprises the amino acid sequence as set forth in SEQ ID NO: 13; and
(b) the light chain variable region comprises three complementarity determining regions (CDRs), $V_L$ CDR1, $V_L$ CDR2 and $V_L$ CDR3, and
wherein $V_L$ CDR1 comprises the amino acid sequence as set forth in SEQ ID NO: 14, $V_L$ CDR2 comprises the amino acid sequence as set forth in SEQ ID NO: 15 and $V_L$ CDR3 comprises the amino acid sequence as set forth in SEQ ID NO: 16, and
wherein the monoclonal antibody specifically binds to a single-chain type IV collagen polypeptide.

4. The monoclonal antibody according to claim 2, wherein the monoclonal antibody recognizes an epitope containing the amino acid sequence as set forth in SEQ ID NO: 41.

5. A monoclonal antibody, comprising:
a heavy chain variable region ($V_H$), and a light chain variable region ($V_L$), wherein
(a) the heavy chain variable region comprises three complementarity determining regions (CDRs), $V_H$ CDR1, $V_H$ CDR2 and $V_H$ CDR3, and
wherein $V_H$ CDR1 comprises the amino acid sequence as set forth in SEQ ID NO: 5 or the amino acid sequence as set forth in SEQ ID NO: 11, $V_H$ CDR2 comprises the amino acid sequence as set forth in SEQ ID NO: 6 or the amino acid sequence as set forth in SEQ ID NO: 12, and $V_H$ CDR3 comprises the amino acid sequence as set forth in SEQ ID NO: 7 or the amino acid sequence as set forth in SEQ ID NO: 13; and
(b) the light chain variable region comprises three complementarity determining regions (CDRs), $V_L$ CDR1, $V_L$ CDR2 and $V_L$ CDR3, and
wherein $V_L$ CDR1 comprises the amino acid sequence as set forth in SEQ ID NO: 8 or the amino acid sequence as set forth in SEQ ID NO: 14, $V_L$ CDR2 comprises the amino acid sequence as set forth in SEQ ID NO: 9 or the amino acid sequence as set forth in SEQ ID NO: 15, and $V_L$ CDR3 comprises the amino acid sequence as set forth in SEQ ID NO: 10 or the amino acid sequence as set forth in SEQ ID NO: 16.

6. The monoclonal antibody according to claim 5, wherein the monoclonal antibody is humanized.

7. A pharmaceutical drug, comprising the monoclonal antibody according to claim 2.

8. A therapeutic drug for tumor, comprising the monoclonal antibody according to claim 2.

9. The therapeutic drug for tumor according to claim 8, wherein the tumor is tumor containing cancer cells expressing a single-chain type IV collagen polypeptide.

10. A partial structure of the monoclonal antibody according to claim 2,
wherein the partial structure contains a variable region of the monoclonal antibody,
wherein the variable region comprises a heavy chain variable region ($V_H$), and a light chain variable region ($V_L$), wherein
(a) the heavy chain variable region comprises three complementarity determining regions (CDRs), $V_H$ CDR1, $V_H$ CDR2 and $V_H$ CDR3, and
wherein $V_H$ CDR1 comprises the amino acid sequence as set forth in SEQ ID NO: 5, $V_H$ CDR2 comprises the amino acid sequence as set forth in SEQ ID NO: 6 and $V_H$ CDR3 comprises the amino acid sequence as set forth in SEQ ID NO: 7; and (b) the light chain variable region comprises three complementarity determining regions (CDRs), $V_L$ CDR1, $V_L$ CDR2 and $V_L$ CDR3, and wherein $V_L$ CDR1 comprises the amino acid sequence as set forth in SEQ ID NO: 8, wherein $V_L$ CDR2 comprises the amino acid sequence as set forth in SEQ ID NO: 9 and wherein $V_L$ CDR3 comprises the amino acid sequence as set forth in SEQ ID NO: 10.

11. A partial structure of the monoclonal antibody according to claim 3, wherein the partial structure contains a variable region of the monoclonal antibody, wherein the variable region comprises a heavy chain variable region ($V_H$), and a light chain variable region ($V_L$), wherein (a) the heavy chain variable region comprises three complementarity determining regions (CDRs), $V_H$ CDR1, $V_H$ CDR2 and $V_H$ CDR3, and wherein $V_H$ CDR1 comprises the amino acid sequence as set forth in SEQ ID NO: 11, $V_H$ CDR2 comprises the amino acid sequence as set forth in SEQ ID NO: 12 and $V_H$ CDR3 comprises and the amino acid sequence as set forth in SEQ ID NO: 13; and (b) the light chain variable region comprises three complementarity determining regions (CDRs), $V_L$ CDR1, $V_L$ CDR2 and $V_L$ CDR3, and wherein $V_L$ CDR1 comprises the amino acid sequence as set forth in SEQ ID NO: 14, wherein $V_L$ CDR2 comprises the amino acid sequence as set forth in SEQ ID NO: 15 and wherein $V_L$ CDR3 comprises and the amino acid sequence as set forth in SEQ ID NO: 16.

12. The monoclonal antibody according to claim 3, wherein the monoclonal antibody recognizes an epitope containing the amino acid sequence as set forth in SEQ ID NO: 41.

13. A pharmaceutical drug, comprising the monoclonal antibody according to claim 3.

14. A therapeutic drug for tumor, comprising the monoclonal antibody according to claim 3.

* * * * *